United States Patent [19]

Eidenschink et al.

[11] Patent Number: 4,818,431

[45] Date of Patent: Apr. 4, 1989

[54] LIQUID CRYSTAL DIELECTRIC

[75] Inventors: Rudolf Eidenschink, Münster; Joachim Krause, Dieburg; Peter Fuss, Mühltal-Traisa, all of Fed. Rep. of Germany

[73] Assignee: Merck Patent Gesellschaft mit beschrankter Haftung, Darmstadt, Fed. Rep. of Germany

[21] Appl. No.: 933,953

[22] Filed: Nov. 24, 1986

Related U.S. Application Data

[63] Continuation of Ser. No. 583,507, Feb. 24, 1984, abandoned.

[30] Foreign Application Priority Data

Feb. 28, 1983 [DE] Fed. Rep. of Germany ....... 3306960

[51] Int. Cl.[4] .................. G02F 1/13; C09K 19/34; C07D 309/30; C07D 309/04; C07D 309/08; C07D 407/02; C07D 405/06; C07D 405/112
[52] U.S. Cl. ................. 252/299.61; 252/299.5; 350/350 R; 544/242; 544/295; 544/298; 544/315; 544/316; 544/318; 544/333; 544/334; 544/335; 546/187; 546/205; 546/206; 546/207; 549/273; 549/291; 549/292; 549/293; 549/356; 549/370; 549/414; 549/415; 549/416; 549/417; 549/419; 549/420; 549/423; 549/425; 549/426; 549/427; 549/428
[58] Field of Search ............... 549/291, 292, 293, 273, 549/414, 415, 416, 417, 419, 420, 423, 426, 427, 428, 356; 250/350 R, 350 S; 252/299.61, 299.5

[56] References Cited

U.S. PATENT DOCUMENTS

| | | | |
|---|---|---|---|
| 3,621,035 | 11/1971 | Lakodey et al. | 260/343 |
| 3,825,572 | 7/1974 | Venrooy . | |
| 4,113,749 | 9/1978 | Simon | 560/51 |
| 4,287,206 | 9/1981 | Simon et al. | 424/279 |
| 4,325,830 | 4/1982 | Sethofer | 252/299.61 |
| 4,335,011 | 6/1982 | Sethofer | 252/299.61 |
| 4,335,012 | 6/1982 | Sorkim | 252/299.61 |
| 4,348,324 | 9/1982 | Demus et al. | 252/299.61 |
| 4,388,104 | 6/1983 | Powell et al. | 549/397 |
| 4,486,332 | 12/1984 | Demus et al. | 252/299.61 |
| 4,512,636 | 4/1985 | Andrews et al. | 252/299.61 |
| 4,521,327 | 6/1985 | Demus et al. | 252/299.61 |
| 4,659,502 | 4/1987 | Fearon et al. | 252/299.61 |

FOREIGN PATENT DOCUMENTS

| | | | |
|---|---|---|---|
| 3322982 | 1/1985 | Fed. Rep. of Germany | 252/299.61 |
| 3405914 | 8/1985 | Fed. Rep. of Germany | 252/299.61 |
| 55149372 | 11/1080 | Japan | 252/299.61 |
| 5716879 | 1/1982 | Japan | 252/299.61 |
| 5785882 | 5/1982 | Japan | 252/299.61 |

OTHER PUBLICATIONS

Kohne, B., Symthesen und Mesomorphe Eigenschaften Neuartiger, Thermotroper Flussigkristalle, Dissertation, Technische Universitat, Berlin, pp. 83–84 (1981).
C. A., vol 102:95286; (1985), Citing Isaev, O. I., et al., Azerb. Khim. Zh., vol. 6, pp. 57–62 (1983).
Demus, D., et al., Flussige Kristalle in Tabellen II, VEB Deutscher Verlag fur Grummstoffimoustrie, Leipzig pp. 362–363 (1984).

Primary Examiner—Teddy S. Gron
Attorney, Agent, or Firm—Millen & White

[57] ABSTRACT

New tetrahydropyran derivatives of the formula I

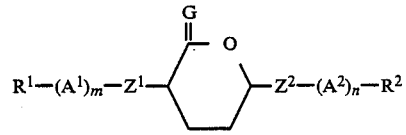

in which G is $H_2$ or =O, $R^1$ and $R^2$ are each an alkyl group having 1–10 C atoms, it also being possible for one or two $CH_2$ groups to be replaced by O atoms, or are F, Cl, Br or CN, $R^2$ is also H, $A^1$ and $A^2$ are each 1,4-phenylene, 1,4-cyclohexylene, 1,3-dioxane-2,5-diyl, piperidine-1,4-diyl, 1,4-bicyclo[2.2.2]octylene or pyrimidine-2,5-diyl groups which are unsubstituted or substituted by 1–4 F atoms, $Z^1$ and $Z^2$ are each —CO—O—, —O—CO—, —$CH_2CH_2$—, —$OCH_2$—, —$CH_2O$—, or a single bond, m and n are each 0, 1, 2 or 3, but (m+n) is at least 1 and at most 3, it being possible, when m is 2 or 3, for the group $A^1$ and, when n is 2 or 3, for the groups $A^2$ each to be identical or different from one another, and the acid addition salts of those among these compounds which are basic, are suitable for use as components in liquid-crystal dielectrics.

17 Claims, No Drawings

LIQUID CRYSTAL DIELECTRIC

This application is a continuation of U.S. Ser. No. 583,507, filed on Feb. 24, 1984, now abandoned.

BACKGROUND OF THE INVENTION

This invention relates to new liquid crystalline compounds.

Compounds similar to those of this invention are disclosed in European Patent Specification 19,665. However, in contrast to the present compounds, those mentioned in this patent contain no tetrahydropyran rings.

SUMMARY OF THE INVENTION

It is an object of this invention to provide new liquid crystalline compounds, or mesogenic compounds, useful as components of liquid crystalline dielectrics.

Upon further study of the specification and appended claims, further objects and advantages of this invention will become apparent to those skilled in the art.

These objects have been achieved by providing new tetrahydropyrans of the Formula I

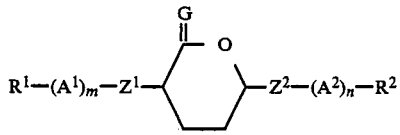

in which G is $H_2$ or =O; $R^1$ and $R^2$ are each independently an alkyl group having 1–10 C atoms, it also being possible for one or two non-adjacent $CH_2$ groups thereof to be replaced by O atoms, or are F, Cl, Br or CN; $R^2$ can also be H; $A^1$ and $A^2$ are each 1,4-phenylene, 1,4-cyclohexylene, 1,3-dioxane-2,5-diyl, piperidine-1,4-diyl, 1,4-bicyclo[2.2.2]octylene or pyrimidine-2,5-diyl each of which is unsubstituted or substituted by 1–4 F atoms; $Z^1$ and $Z^2$ are each independently —CO—O—, —O—CO—, —$CH_2CH_2$—, —$OCH_2$—, —$CH_2O$—, of a single bond; m and n each independently is 0, 1, 2 or 3, but (m+n) is at least 1 and at most 3, it being possible, when m is 2 or 3, for the groups $A^1$ and, when n is 2 or 3, for the groups $A^2$ each independently to be identical or different from one another, and the acid addition salts of those compounds among these which are basic.

For reasons of simplicity, in the following text "A" denotes 2-G-tetrahydropyran-3,6-diyl, "Phe" denotes 1,4-phenylene; "Cy" denotes 1,4-cyclohexylene; "Dio" denotes 1,3-dioxane-2,5-diyl; "Bi" denotes bicyclo[2.2.2]octylene; "Pip" denotes piperidine-1,4-diyl; and "Pyr" denotes pyrimidine-2,5-diyl; it being possible for these groups, in particular the 1,4-phenylene group, to be unsubstituted or (apart from A) to be substituted by 1–4 fluorine atoms.

The compounds of Formula I can be used like similar compounds as components of liquid-crystal dielectrics, in particular for displays which are based on the principle of the twisted cell, the guest-host effect, the effect of deformation of aligned phases, the effect of dynamic scattering or the 2-frequency process.

DETAILED DISCUSSION

It has been found that the compounds of the Formula I are excellently suitable for use as components of liquid-crystal dielectrics. In particular, it is possible with their aid to prepare stable liquid-crystal phases which have strongly negative or positive dielectric anisotropy, and thus a low threshold or control voltage for electrooptical effects, widely variable optical anistotropy and ocmparatively low viscosity.

In addition, providing the compounds of the Formula I considerably extends, in a very general way, the range of liquid-crystal substances which are suitable, from a variety of viewpoints of application technology, for the preparation of nematic mixtures. In one aspect, this invention excludes compounds wherein, when -$(A^2)_n$-$R^2$ is OR wherein R is alkyl (and optionally also H) and $Z^1$ and $Z^2$ are single bonds and G is $H_2$, $R^1$-$(A^1)_m$- is 4-cycanophenyl, 4-alkylphenyl (and, optionally, 4-alkoxyphenyl) or 4-alkylcyclohexyl (and, optionally, 4-alkoxycyclohexyl), inter alia.

The compounds of the formula I have a wide range of applications. Depending on the selection of the substituents, these compounds can be used as the base materials of which liquid-crystal dielectrics are mainly composed; however, it is also possible to add to compounds of the formula I liquid-crystal base materials belonging to other classes of compounds, in order, for example, considerably to affect the dielectric and/or optical anisotropy of such a dielectric. The compounds of the formula I are also suitable as intermediates for the preparation of other substances which can be used as constituents of liquid-crystal dielectrics.

In the pure state, the compounds of the formula I are colorless and form liquid-crystal mesophases in a temperature range which is advantageously situated for electrooptical use. They are very stable to chemicals, heat and light.

Thus the invention relates to compounds of the formula I and to a process for their preparation, characterised in that a compound which otherwise corresponds to formula I but, in place of H atoms, contains one or more reducible groups and/or C—C bonds, is treated with a reducing agent, or in that a compound of the formula II

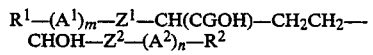

in which G, $R^1$, $R^2$, $A^1$, $A^2$, $Z^1$, $Z^2$, m and n have the indicated meanings, or one of its reactive derivatives is cyclized, or in that a compound of the formula III

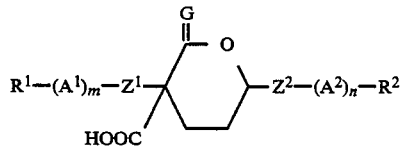

in which G, $R^1$, $R^2$, $A^1$, $A^2$, $Z^1$, $Z^2$, m and n have the indicated meanings, is decarboxylated, or in that, for the preparation of compounds of the formula I in which $R^1$ and/or $R^2$ are F, CL, Br or CN, the diazonium group in an appropriate diazonium salt is replaced by F, Cl, Br or CN, or in that, for the preparation of esters of the formula I (in which $Z^1$ and/or $Z^2$ is —CO—O— or —O—CO—), an appropriate carboxylic acid or one of its reactive derivatives is reacted with an appropriate alcohol or one of its reactive derivatives, or in that, for the preparation of dioxane derivatives of the formula I (in which $A^1$ and/or $A^2$ is 1,3-dioxane-2,5-diyl), an appropriate aldehyde is reacted with an appropriate diol, or in that, for the preparation of nitriles of the formula I (in which $R^1$ and/or $R^2$ is CN), an appropriate carboxamide is dehydrated or an appropriate carbonyl halide is reacted with sulfamide, or in that, for the preparation of ethers of the formula I (in which $R^1$ and or $R^2$ are alkyl chains, in which one or two $CH_2$ groups are replaced by O atoms, and/or $Z^1$ and/or $Z^2$ are $-OCH_2-$ or $-CH_2O-$ groups), an appropriate hydroxy compound is etherified, and/or in that, where appropriate, a chloro or bromo compound of the formula I (in which $R^1$ and/or $R^2$ is Cl or Br) is reacted with a cyanide, and/or in that, where appropriate, a base of the formula I is converted, by treatment with an acid, into one of its acid addition salts, or in that, where appropriate, a compound of the formula I is liberated from one of its acid addition salts by treatment with a base.

Furthermore, the invention relates to the use of the compounds of the formula I as components in liquid-crystal dielectrics. The invention also relates to liquid-crystal dielectrics containing at least one compound of the formula I and to electrooptical display elements which contain dielectrics of this type.

In the preceding and following text, unless otherwise expressly noted, G, $R^1$, $R^2$, $A^1$, $A^2$, $Z^1$, $Z^2$, m and n have the indicated meaning.

Accordingly, the compounds of the formula I comprise compounds of the part formulae Ia and Ib (each having two rings), Ic to Ie (each having three rings) and If to Ii (each having four rings):

| | |
|---|---|
| $R^1-A^1-Z^1-A-Z^2-R^2$ | Ia |
| $R^1-Z^1-A-Z^2-A^2-R^2$ | Ib |
| $R^1-(A^1)_2-Z^1-A-Z^2-R^2$ | Ic |
| $R^1-A^1-Z^1-A-Z^2-A^2-R^2$ | Id |
| $R^1-Z^1-A-Z^2-(A^2)_2-R^2$ | Ie |
| $R^1-(A^1)_3-Z^1-A-Z^2-R^2$ | If |
| $R^1-(A^1)_2-Z^1-A-Z^2-A^2-R^2$ | Ig |
| $R^1-A^1-Z^1-A-Z^2-(A^2)_2-R^2$ | Ih |
| $R^1-Z^1-A-Z^2-(A^2)_3-R^2$ | Ii. |

The preferred compounds of the part formulae Ia and Ib comprise those of the part formulae Iaa to Iaf and Iba to Ibf

| | |
|---|---|
| $R^1-Phe-Z^1-A-Z^2-R^2$ | Iaa |
| $R^1-Cy-Z^1-A-Z^2-R^2$ | Iab |
| $R^1-Dio-Z^1-A-Z^2-R^2$ | Iac |
| $R^1-Pip-Z^1-A-Z^2-R^2$ | Iad |
| $R^1-Bi-Z^1-A-Z^2-R^2$ | Iae |
| $R^1-Pyr-Z^1-A-Z^2-R^2$ | Iaf |
| $R^1-Z^1-A-Z^2-Phe-R^2$ | Iba |
| $R^1-Z^1-A-Z^2-Cy-R^2$ | Ibb |
| $R^1-Z^1-A-Z^2-Dio-R^2$ | Ibc |
| $R^1-Z^1-A-Z^2-Pip-R^2$ | Ibd |
| $R^1-Z^1-A-Z^2-Bi-R^2$ | Ibe |
| $R^1-Z^1-A-Z^2-Pyr-R^2$ | Ibf |

Of these, those of the formula Iba are particularly preferred.

Of the compounds of the part formulae Ic to Ii, those of the part formulae Ie and Ii are particularly preferred, specifically those of the part formulae Ica to Iih:

| | |
|---|---|
| $R^1-Phe-Phe-Z^1-A-Z^2-R^2$ | Ica |
| $R^1-Phe-Cy-Z^1-A-Z^2-R^2$ | Icb |
| $R^1-Cy-Phe-Z^1-A-Z^2-R^2$ | Icc |
| $R^1-Cy-Cy-Z^1-A-Z^2-R^2$ | Icd |
| $R^1-Phe-Z^1-A-Z^2-Phe-R^2$ | Ida |
| $R^1-Phe-Z^1-A-Z^2-Cy-R^2$ | Idb |
| $R^1-Cy-Z^1-A-Z^2-Phe-R^2$ | Idc |
| $R^1-Cy-Z^1-A-Z-Cy-R^2$ | Idd |
| $R^1-Z^1-A-Z^2-Phe-Phe-R^2$ | Iea |
| $R^1-Z^1-A-Z^2-Phe-Cy-R^2$ | Ieb |
| $R^1-Z^1-A-Z^2-Cy-Phe-R^2$ | Iec |
| $R^1-Z^1-A-Z^2-Cy-Cy-R^2$ | Ied |
| $R^1-Phe-Phe-Phe-Z^1-A-Z^2-R^2$ | Ifa |
| $R^1-Phe-Phe-Cy-Z^1-A-Z^2-R^2$ | Ifb |
| $R^1-Phe-Cy-Phe-Z^1-A-Z^2-R^2$ | Ifc |
| $R^1-Phe-Cy-Cy-Z^1-A-Z^2-R^2$ | Ifd |
| $R^1-Cy-Phe-Phe-Z^1-A-Z^2-R^2$ | Ife |
| $R^1-Cy-Phe-Cy-Z^1-A-Z^2-R^2$ | Iff |
| $R^1-Cy-Cy-Phe-Z^1-A-Z^2-R^2$ | Ifg |
| $R^1-Cy-Cy-Cy-Z^1-A-Z^2-R^2$ | Ifh |
| $R^1-Phe-Phe-Z^1-A-Z^2-Phe-R^2$ | Iga |
| $R^1-Phe-Phe-Z^1-A-Z^2-Cy-R^2$ | Igb |
| $R^1-Phe-Cy-Z^1-A-Z^2-Phe-R^2$ | Igc |
| $R^1-Phe-Cy-Z^1-A-Z^2-Cy-R^2$ | Igd |
| $R^1-Cy-Phe-Z^1-A-R^2-Phe-R^2$ | Ige |
| $R^1-Cy-Phe-Z^1-A-Z^2-Cy-R^2$ | Igf |
| $R^1-Cy-Cy-Z^1-A-Z^2-Phe-R^2$ | Igg |
| $R^1-Cy-Cy-Z^1A-Z^2-Cy-R^2$ | Igh |
| $R^1-Phe-Z^1-A-Z^2-Phe-Phe-R^2$ | Iha |
| $R^1-Phe-Z^1-A-Z^2-Phe-Cy-R^2$ | Ihb |
| $R^1-Phe-Z^1-A-Z^2-Cy-Phe-R^2$ | Ihc |
| $R^1-Phe-Z^1-A-Z^2-Cy-Cy-R^2$ | Ihd |

$R^1$—Cy—$Z^1$—A—$Z^2$—Phe—Phe—$R^2$   Ihe $R^1$—Cy—$Z^1$—A—$Z^2$—Phe—Cy—$R^2$   Ihf $R^1$—Cy—$Z^1$—A—$Z^2$—Cy—Phe—$R^2$   Ihg $R^1$—Cy—$Z^1$—A—$Z^2$—Cy—Cy—$R^2$   Ihh $R^1$—$Z^1$—A—$Z^2$—Phe—Phe—Phe—$R^2$   Iia $R^1$—$Z^1$—A—$Z^2$—Phe—Phe—Cy—$R^2$   Iib $R^1$—$Z^1$—A—$Z^2$—Phe—Cy—Phe—$R^2$   Iic $R^1$—$Z^1$—A—$Z^2$—Phe—Cy—Cy—$R^2$   Iid $R^1$—$Z^1$—A—$Z^2$—Cy—Phe—Phe—$R^2$   Iie $R^1$—$Z^1$—A—$Z^2$—Cy—Phe—Cy—$R^2$   Iif $R^1$—$Z^1$—A—$Z^2$—Cy—Cy—Phe—$R^2$   Iig $R^1$—$Z^1$—A—$Z^2$—Cy—Cy—Cy—$R^2$   Iih.

The compounds of the part formulae Iea and Iib are particularly preferred.

In the compounds of the formulae given above and below, $R^1$ and $R^2$ are preferably alkyl, but also alkoxy (especially when these radicals are located on a Phe group) or another oxaalkyl group.

$A^1$ and $A^2$ are preferably Cy or Phe, but also preferably Dio or Pip; the compound of the formula I preferably contains not more than one of the radicals Dio, Pip, Bi or Pyr.

G is preferably 2H atoms.

$Z^1$ and $Z^2$ are preferably single bonds as a second preference they are —CO—O— or —O—CO— groups.

m is preferably 0, and n is preferably 1.

In the compounds of the formulae given above and below, it is possible for the alkyl radicals, in which it is also possible for one ("alkoxy" or "oxaalkyl") or two ("alkoxyalkoxy" or "dioxaalkyl") $CH_2$ groups to be replaced by O atoms, to be straight-chain or branched. They are preferably straight-chain, have 2, 3, 4, 5, 6 or 7 C atoms and accordingly are preferably ethyl, propyl, butyl, pentyl, hexyl, heptyl, ethoxy, propoxy, butoxy, pentoxy, hexoxy, heptoxy, 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, but also methyl, octyl, nonyl, decyl, methoxy, octoxy, nonoxy, decoxy, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-, 1,4- or 2,4-dioxapentyl, 1,3-, 1,4-, 1,5-, 2,4-, 2,5- or 3,5-dioxahexyl or 1,3-, 1,4-, 1,5-, 1,6-, 2,4-, 2,5-, 2,6-, 3,5-, 3,6- or 4,6-dioxaheptyl.

Compounds of the formulae I and Ia to Iih having branched wing groups $R^1$ and $R^2$ can occasionally be of importance because of improved solubility in the customary liquid-crystal base materials, but are especially of importance as chiral doping agents when they are optically active. Branched groups of this type do not, as a rule, contain more than one chain branching. Preferred branched radicals $R^1$ and $R^2$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl and 3-oxa-4-methylpentyl.

Preferred compounds among those of the formulae I and Ia to Iih are those in which at least one of the radicals contained therein has one of the meanings indicated as being preferred. Particularly preferred smaller groups of compounds are those of the formulae Ij to Iq $R^1$—A—$Z^2$—$A^2$—$R^2$   Ij $R^1$—A—$A^2$—$R^2$   Ik $R^1$—A—Phe—$R^2$   Il $R^1$—A—Phe—CN   Im $R^1$—A—$(A^2)_2$—$R^2$   In $R^1$—A—Phe—Phe—$R^2$   Io $R^1$—A—$(A^2)_3$—$R^2$   Ip $R^1$—A—Phe—Phe—Cy—$R^2$   Iq Those of the abovementioned formulae which contain one or more of the groups Dio, Pip and/or Pyr, each include the two possible 2,5- and 1,4-positional isomers. Thus, for example, the part formula Iac includes 2-$R^1$-5-(A-$R^2$)-1,3-dioxanes and 2-(A-$R^2$)-5-$R^1$-1,3-dioxanes, and part formula Iad includes 1-$R^1$-4-(A-$R^2$)-piperidines and 1-(A-$R^2$)-4-$R^1$-piperidines.

All the compounds mentioned which contain cyclohexane, 1,3-dioxane and/or tetrahydropyran rings can exist as cis and trans forms and as mixtures.

Those compounds in which the substituents are in the trans position with respect to one another are preferred. As a rule, these are more stable; in many cases, the cis compounds (or mixtures) can be converted into the trans compounds by treatment with a base, for example with K tert.-butylate in an inert solvent, such as dimethyl sulfoxide.

The compounds of the formula I are prepared by methods known per se, as are described in the literature (for example in the standard works, such as Houben-Weyl, Methoden der Organischen Chemie (Methods of Organic Chemistry), Georg-Thieme-Verlag, Stuttgart), namely under reaction conditions which are known and suitable for the reactions mentioned. It is also possible to make use of variants of these reactions which are known per se but which are not mentioned here in detail.

The starting materials can, if desired, also be formed in situ, in such a manner that they are not isolated from the reaction mixture, but are immediately reacted further to give the compounds of the formula I.

Thus, the compounds of the formula I can be prepared by reducing a compound which otherwise corresponds to the formula I, but contains one or more reducible groups and/or C—C bonds in place of H atoms.

Suitable reducible groups are preferably carbonyl groups, especially keto groups, but also, for example, free or esterified hydroxyl groups or halogen atoms bonded to aromatics. Preferred starting materials for the reduction correspond tot he formula I, but can contain a dihydropyran ring in place of the tetrahydropyran ring, and/or a cyclohexene ring or cyclohexanone ring in place of a cyclohexane ring, and/or a —CH=CH— group or a —$CH_2$—CO— group in place of a —$CH_2CH_2$— group.

The reduction is preferably carried out by catalytic hydrogenation at temperatures between about 0° and about 200° and under pressures between about 1 and 200 bar, in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane.

Suitable catalysts are preferably noble metals, such as Pt or Pd, which can be employed in the form of oxides (for example $PtO_2$, PdO) or a support (for example Pd on charcoal, calcium carbonate or strontium carbonate) or in the finely divided form (for example Pt black).

The compounds of the formula I are obtained in a particularly advantageous manner by cyclizing the compounds of the formula II or their reactive derivatives. Lactonization of the hydroxyacids of the formula II (G=O) leads to the lactones of the formula I (G=O); dehydration with cyclization of the diols of the formula II (G=H$_2$) leads to the tetrahydropyrans of the formula I (G=H$_2$).

The starting materials of the formula II can be obtained, for example, by reaction of malonic esters of the formula $R^1$—$(A^1)_m$—$Z^1$—$CH(COOalkyl)_2$ with halides of the formula Hal—$CH_2CH_2$—CO—$Z^2$—$(A^2)_n$—$R^2$ (Hal=Cl or Br) to give compounds of the formula $R^1$—$(A^1)_m$—$Z^1$—$C(COOalkyl)_2$—$CH_2CH_2$—CO—$Z^2$—$(A^2)_n$—$R^2$, hydrolysis and decarboxylation to give ketoacids of the formula $R^1$—$(A^1)_m$—$Z^1$—$CH(COOH)$—$CH_2CH_2$—CO—$Z^2$—$(A^2)_n$—$R^2$ and reduction to give the hydroxyacids II (G=O), which are usually not isolated but lactonize spontaneously, or to give the diols II (G=H$_2$).

Examples of suitable reactive derivatives of the compounds of the formula II are the corresponding halogen derivatives (Hal in place of one or both OH groups), and corresponding reactive esters, for example alkylsulfonates or arylsulfonates, in which the alkyl groups contain, in particular, 1–6, and the aryl groups 6–10, C atoms, for example the mono- or di-methanesulfonates, benzenesulfonates or p-toluenesulfonates of the diols mentioned.

As a rule, the cyclization is carried out at temperatures between about 0° and 250° in the presence or absence of an inert solvent, for example a hydrocarbon, such as benzene, toluene or xylene, an amide, such as dimethylformamide or phosphoric hexamethyltriamide or a sulfoxide, such as dimethyl sulfoxide. As a rule, the lactonization takes place by simply heating to about 150°–250°. The cyclization of the diols is preferably carried out at about 60°–150° in the presence of an acid catalyst, for example a mineral acid, such as sulfuric acid, hydrochloric acid, phosphoric acid or perchloric acid, an organic sulfonic acid, such as benzenesulfonic acid, p-toluenesulfonic acid or naphthalenesulfonic acid, a Lewis acid, such as $BF_3$ or $ZnCL_2$, or an acid salt, such as $NaHSO_4$.

In addition, the compounds of the formula I can be obtained by decarboxylation of the compounds of the formula III. G in these is preferably an O atom. They can be obtained, for example, by reduction of the mentioned ketomalonic esters of the formula $R^1$—$(A^1)_m$—$Z^1$—$C(COOalkyl)_2$—$CH_2CH_2$—CO—$Z^2$—$(A^2)_n$—$R^2$ to give the corresponding hydroxyesters of the formula $R^1$—$(A^1)_m$—$Z^1$—$C(COOalkyl)_2$—$CH_2CH_2$—CHOH—$Z^2$—$(A^2)_n$—$R^2$, which on hydrolysis very readily lactonize to give the valero-lactone-carboxylic acids of the formula III (G=O).

As a rule, the compounds of the formula III are not isolated but are decarboxylated by heating in the absence or in the presence of an inert solvent to temperatures between about 80° and 250°.

Compounds of the formula I in which R1 and/or $R^2$ are F, Cl, Br or CN can also be obtained from the corresponding diazonium salts by replacing the diazonium group by a fluorine, chlorine or bromine atom or by a CN group, for example by the methods of Schiemann or Sandmeyer.

The diazonium salts can be prepared, for example, by nitration of compounds which correspond to the formula I but which contain one (or two) hydrogen atom(s) in place of the radicals $R^1$ and/or $R^2$, reduction to give the corresponding amines and diazotization, for example with $NaNO_2$ or $KNO_2$ in aqueous solution at temperatures between about $-10°$ and $+10°$.

To replace the diazonium group by fluorine, it is possible to diazotize in anhydrous hydrofluoric acid and then heat, or reaction is carried out with tetrafluoroboric acid to give the diazonium tetrafluoroborates which are then decomposed by heat.

Replacement by Cl, Br or CN is preferably achieved by reacting the aqueous solution of diazonium salt with $Cu_2Cl_2$, $Cu_2Br_2$ or $Cu_2(CN)_2$ by the Sandmeyer method.

Esters of the formula I ($Z^1$ and/or $Z^2$=—CO—O— or —O—CO—) can also be obtained by esterifying corresponding carboxylic acids of the formula $R^1$—$(A^1)_m$—COOH, $R^1$—$(A^1)_m$—$Z^1$—A—COOH, $R^2$—$(A^2)_n$—COOH or $R^2$—$(A^2)_n$—$Z^2$—A—COOH (or their reactive derivatives) with alcohols or phenols of the formulae $R^2$—$(A^2)_n$—$Z^2$—A—OH, $R^2$—$(A^2)_n$—OH, $R^1$—$(A^1)_m$—$Z^1$—A—OH or $R^1$—$(A^1)_m$—OH (or their reactive derivatives).

Particularly suitable reactive derivatives of the carboxylic acids mentioned are the acid halides, in particular the chlorides and bromides, but also the anhydrides, for example including mixed anhydrides of the formulae $R^1$—$(A^1)_m$—CO—O—COCH$_3$, $R^1$—$(A^1)_m$—$Z^1$—A—CO—O—COCH$_3$, $R^2$—$(A^2)_n$—CO—O—COCH$_3$ and $R^2$—$(A^2)_n$—$Z^2$—A—CO—O—COCH$_3$, azides or esters, especially alkyl esters having 1–4 C atoms in the alkyl group.

Particularly suitable reactive derivatives of the alcohols and phenols mentioned are the corresponding metal alcoholates or phenolates of the formulae $R^2$—$(A^2)_n$—$Z^2$—A—OM, $R^2$—$(A^2)_n$—OM, $R^1$—$(A^1)_m$—$Z^1$—A—OM and $R^1$—$(A^1)_m$—OM, M being one equivalent of a metal, preferably an alkali metal, such as Na or K.

The esterification is preferably carried out in the presence of an inert solvent. Particularly well suited are ethers, such as diethyl ether, di-n-butyl ether, THF, dioxane or anisole, ketones, such as acetone, butanone or cyclohexanone, amides, such as DMF or phosphoric hexamethyltriamide, hydrocarbons, such as benzene, toluene or xylene, halogenated hydrocarbons, such as carbon tetrachloride or tetrachloroethylene, and sulfoxides, such as dimethyl sulfoxide or sulfolane. Solvents which are immiscible with water can advantageously be used at the same time for removing, by azeotropic distillation, the water formed during the esterification. It is also possible to use, on occasion, an excess of an organic base, for example pyridine, quinoline or triethylamine as the solvent for the esterification. The esterification can also be carried out in the absence of a solvent, for example by simply heating the components in the presence of sodium acetate. The reaction temperature is usually between −50° and +250°, preferably between −20° and +80°. As a rule, the esterification reactions are complete after 15 minutes to 48 hours at these temperatures.

The reaction conditions for the esterification in specific cases largely depend on the nature of the starting materials used. Thus, as a rule, a free carboxylic acid is reacted with a free alcohol or phenol in the presence of a strong acid, for example a mineral acid, such as hydrochloric acid or sulfuric acid. A preferred mode of reaction is to react an anhydride or, in particular, an acid chloride, with an alcohol, preferably in a basic medium, bases which are of importance being, in particular, alkali metal hydroxides, such as sodium or potassium hydroxide, alkali metal carbonates or bicarbonates, such as sodium carbonate, sodium bicarbonate, potassium carbonate or potassium bicarbonate, alkali metal acetates, such as sodium or potassium acetate, alkaline earth metal hydroxides, such as calcium hydroxide, or organic bases, such as triethylamine, pyridine, lutidine, collidine or quinoline. Another preferred embodiment of the esterification comprises initially converting the alcohol or phenol into the sodium or potassium alcoholate or phenolate, respectively, for example by treatment with ethanolic sodium or potassium hydroxide solution, isolating this alcoholate or phenolate and suspending it, together with sodium bicarbonate or potassium carbonate, in acetone or diethyl ether with stirring, and adding a solution of the acid chloride or anhydride in diethyl ether, acetone or DMF to this suspension, preferably at temperatures between about −25° and +20°.

Dioxane derivatives of the formula I (in which one of the groups $A^1$ and/or $A^2$ is a 1,3-dioxane-2,5-diyl group) are preferably prepared by reaction of an appropriate aldehyde, for example of the formulae $R^1—(A^1)_{m-1}—CHO$, $R^1—(A^1)_m—Z^1—A—Z^2—CHO$, $O=CH—(A^1)_{m-1}—Z^1—A—Z^2—(A^2)_n—R^2$ or $O=CH—R^2$ (or one of its reactive derivatives) with an appropriate 1,3-diol, for example of the formulae $(HOCH_2)_2CH—(A^1)_{m-1}—Z^1—A—Z^2—(A^2)_n—R^2$, $(HOCH_2)_2CH—R^2$, $R^1—(A^1)_{m-1}—CH(CH_2OH)_2$ or $R^1—(A^1)_m—Z^1—A—Z^2—CH(CH_2OH)_2$ (or one of its reactive derivatives), preferably in the presence of an inert solvent, such as benzene or toluene, and/or a catalyst, for example a strong acid, such as sulfuric acid, benzenesulfonic or p-toluenesulfonic acid, at temperatures between about 20° and about 150°, preferably between 80° and 120°. Reactive derivatives of the starting materials which are primarily suitable are acetals, for example of the formulae $R^1—(A^1)_{m-1}CH(OR^3)_2$, $R^1—(A^1)_m—Z^1—A—Z^2—CH(OR^3)_2$, $(R^3O)_2CH—(A^1)_{m-1}—Z^1—A—Z^2—(A^2)_n—R^2$, $(R^3O)_2—R^2$, $R^4—CH(OCH_2)_2CH—(A^1)_{m-1}—Z^1—A—Z^2—(A^2)_n—R^2$, $R^4—CH(OCH_2)_2CH—R^2$, $R^1—(A^1)_{m-1}—CH(CH_2O)_2CH—R^4$ or $R^1—(A^1)_m—Z^1—A—Z^1—CH(CH_2O)_2CHR^4$, in which $R^3$ is alkyl having 1–4 C atoms, also two radicals $R^3$ together are alkylene having 2 or 3 C atoms, and $R^4$ is H, alkyl having 1–4 C atoms or phenyl.

Some of the aldehydes and 1,3-diols and their reactive derivatives mentioned are known, and some of them can be prepared without difficulty from compounds known from the literature by standard processes in organic chemistry. For example, the aldehydes can be obtained by oxidation of corresponding alcohols or by reduction of corresponding carboxylic acids or their derivatives, and the diols can be obtained by reduction of corresponding diesters.

For the preparation of nitriles of the formula I (in which $R^1$ and/or $R^2$ are CN), it is possible to dehydrate corresponding amides, for example those in which a $CONH_2$ group is present in place of the radical $R^1$ and/or $R^2$. The amides can be obtained, for example, from corresponding esters or acid halides by reaction with ammonia. Examples of suitable dehydrating agents are inorganic acid chlorides, such as $SOCl_2$, $PCl_3$, $PCl_5$, $POCl_3$, $SO_2Cl_2$ and $COCl_2$, also $P_2O_5$, $P_2S_5$ and $AlCl_3$ (for example as a double compound with NaCl), aromatic sulfonic acids and sulfonyl halides. This reaction can be carried out in the presence or absence of an inert solvent at temperatures between about 0° and 150°; examples of suitable solvents are bases, such as pyridine or triethylamine, aromatic hydrocarbons, such as benzene, toluene or xylene, or amides, such as DMF.

To prepare the abovementioned nitriles of the formula I, it is also possible to react corresponding acid halides, preferably the chlorides, with sulfamide, preferably in an inert solvent, such as tetramethylene sulfone, at temperatures between about 80° and 150°, preferably at 120°. After working up as usual, the nitriles can be directly isolated.

Ethers of the formula I (in which $R^1$ and/or $R^2$ are an alkyl chain in which one or two $CH_2$ groups are replaced by O atoms, and/or in which $Z^1$ and/or $Z^2$ are a $—OCH_2—$ or a $—CH_2O—$ group), can be obtained by etherification of corresponding hydroxyl compounds, preferably corresponding phenols, the hydroxyl compound preferably initially being converted into an appropriate metal derivative, for example by treatment with NaOH, KOH, $Na_2CO_3$ or $K_2CO_3$ into the corresponding alkali metal alcoholate or alkali metal phenolate. The latter can then be reacted with the appropriate alkyl halide, sulfonate or dialkyl sulfate, preferably in an inert solvent, such as acetone, DMF or dimethyl sulfoxide, or in an excess of aqueous or aqueous-alcoholic NaOH or KOH at temperatures between about 20° and 100°.

For the preparation of nitriles of the formula I (in which $R^1$ and/or $R^2$ are CN), it is also possible to react appropriate chlorine or bromine compounds of the formula I (in which $R^1$ and/or $R^2$ are Cl or Br) with a cyanide, preferably with a metal cyanide, such as NaCN, KCN or $Cu_2(CN)_2$, for example in the presence of pyridine in an inert solvent, such as DMF or N-methylpyrrolidone, at temperatures between 20° and 200°.

A base of the formula I can be converted with an acid into the relevant acid addition salt. It is possible to use inorganic acids for this conversion, for example sulfuric acid, nitric acid, hydrogen halide acids, such as hydrochloric acid or hydrobromic acid, phosphoric acids, such as orthophosphoric acid, and sulfamic acid, but also organic acids, especially aliphatic, alicyclic, aralipathic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalenemono- and -disulfonic acids and lauryl sulfuric acid.

Conversely, it is possible to liberate the base of the formula I from an acid addition salt of a compound of the formula I by treatment with a base, for example with a strong inorganic base, such as KOH or NaOH.

The dielectrics according to the invention comprise 2 to 20, preferably 3 to 12, components, including at least one compound of the formula I. The other constituents are preferably selected from the nematic or nematogenic substances, especially the known substances belonging to the classes comprising the azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-biscyclohexylbenzenes, 4,4'-biscyclohexylbiphenyls, phenylpyrimidines or cyclohexylpyrimidines, phenyldioxanes or cyclohexyldioxanes, optionally halogenated stilbenes, benzyl phenyl ethers, benzyl cyclohexyl ethers, cyclohexylmethyl phenyl ethers, cyclohexylmethyl cyclohexyl ethers, tolanes, substituted cinnamic acids, decalins, perhydrophenanthrenes, bicyclooctanes, 1,2-dicyclohexylethanes and 1-cyclohexyl-2-phenylethanes.

The most important compounds which are suitable as constituents of liquid-crystal dielectrics of this type can be characterized by the formula IV,

R'—X—Y—Z—R''      IV in which X and Z are each a carbocyclic or heterocyclic ring system composed of the group formed from 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, dihydronaphthalene and tetrahydronaphthalene, quinazoline and tetrahydroquinazoline, Y is

| —CH=CH— | —N(O)=N— |
|---|---|
| —C=CQ— | —CH=N(O)— |
| —C≡C— | —CH$_2$—CH$_2$— |
| —CO—O— | —CH$_2$—O— |
| —CO—S— | —CH$_2$—S— |
| —CH=N— | —COO—Phe-COO— | or a C—C single bond, Q is halogen, preferably chlorine, or —CN, and R' and R'' are alkyl, alkoxy, alkanoyloxy or alkoxycarbonyloxy having up to 18, preferably up to 8, carbon atoms, or one of these radicals is also CN, NC, NO$_2$, CF$_3$, F, Cl or Br.

R' and R'' in most of these compounds are different, one of these radicals usually being an alkyl or alkoxy group. However, other variants of the scheduled substituents are also customary. Many of such substances or mixtures thereof are obtainable commercially.

The dielectrics according to the invention contain about 0.1 to 100, preferably 10 to 100, % of one or more compounds of the formula I.

The preparation of dielectrics according to the invention is carried out in a manner known per se. As a rule, the components are dissolved in one another, preferably at elevated temperature.

The liquid-crystal dielectrics according to the invention can be modified by suitable additives in such a manner that they can be used in all types of liquid-crystal display elements hitherto disclosed.

Additives of these types are well known to those skilled in the art and are described in detail in the literature. For example, it is possible to add conducting salts, preferably ethyldimethyldodecylammonium 4-hexyloxybenzoate, tetrabutylammonium tetraphenylboranate, or complex salts of crown ethers (compare, for example, I. Haller et al., Mol. Cryst. Liq. Cryst. Volume 24, pages 249–258 (1973)) to improve the conductivity, or to add dichroic dyestuffs to prepare coloured guest-host systems, or to add substances to modify the dielectric anisotropy, the viscosity and/or the orientation of the nematic phases. Substances of these types are described, for example, in German Offenlegungsschriften 2,209,127, 2,240,864, 2,321,632, 2,338,281, 2,450,088, 2,637,430, 2,853,728 and 2,902,177.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional will be applicable to the preparation of the corresponding compounds of this invention. In all preparative methods, all starting materials are known or readily preparable from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples and in the preceding text, all temperatures are set forth uncorrected in degrees Celsius and all parts and percentages are by weight, unless otherwise indicated.

In the examples, m.p. is the melting point and c.p. is the clear point of a liquid crystal substance. "Usual work-up" means: water is added, the mixture is extracted with methylene chloride, the phases are separated, and the organic phase is dried, evaporated and the product is purified by crystallization and/or chromatography.

EXAMPLE 1

A solution of 23.4 g of 3-(p-methoxybenzoylmethyl)-tetrahydropyran (obtainable by reaction of 2,3-dihydro-4H-pyran with HBr to give 3-bromotetrahydropyran, reaction with diethyl malonate to give diethyl tetrahydropyran-3-ylmalonate, hydrolysis, decarboxylation, reaction with SOCl$_2$ to give tetrahydropyran-3-acetyl chloride, and reaction with anisole in the presence of AlCl$_3$) in 500 ml of THF is hydrogenated on 5 g of 10% Pd/C at 40° and 1 bar until 0.2 mole of H$_2$ has been taken up. The mixture is filtered, evaporated and 3-(2-p-methoxyphenylethyl)tetrahydropyran is obtained.

The following can be obtained analogously:
3-(2-p-Ethoxyphenylethyl)-tetrahydropyran
3-(2-p-Tolylethyl)-tetrahydropyran
3-(2-p-Ethylphenylethyl)-tetrahydropyran
3-(2-p-Propylphenylethyl)-tetrahydropyran
3-(2-p-Butylphenylethyl)-tetrahydropyran 3-(2-p-Pentylphenylethyl)-tetrahydropyran
3-(2-p-Hexylphenylethyl)-tetrahydropyran.

EXAMPLE 2

10 g of 3-p-propylphenyl-4,5-dihydro-6H-pyran (obtainable by hydrolysis of 3-bromotetrahydropyran to give 3-hydroxytetrahydropyran, reaction with p-propylphenyl magnesium bromide to give 3-p-propylphenyl-3-hydroxy-tetrahydropyran followed by dehydration) are dissolved in 100 ml of ethanol and hydrogenated to standstill on 2 g of Raney nickel at 20° under 3 atmospheres. After decantation and evaporation, 3-p-propylphenyltetrahydropyran is obtained.

The following can be obtained analogously:
3-p-Tolyl-tetrahydropyran
3-p-Ethylphenyl-tetrahydropyran
3-p-Butylphenyl-tetrahydropyran
3-p-Pentylphenyl-tetrahydropyran
3-p-Methoxyphenyl-tetrahydropyran
3-p-Ethoxyphenyl-tetrahydropyran.

EXAMPLE 3

A solution of 29.4 g of 4-hydroxymethyl-1-p-ethoxyphenyl-1-nonanol [obtainable by reaction of diethyl 2-pentylmalonate (boiling point 127°/13 mbar) with ethyl 3-bromopropionate to give diethyl 2-carboethoxy-2-pentylglutarate (boiling point 160°/0.4 mbar), hydrolysis and decarboxylation to give 2-pentylglutaric acid, heating to form the anhydride (boiling point 120°/0.7 mbar), reaction with phenetol/AlCl$_3$ to give 4-p-ethoxybenzoyl-2-pentylbutyric acid (m.p. 61°) and reduction with LiAlH$_4$] and 1 g of p-toluenesulfonic acid in 400 ml of benzene is boiled under a water separator for 6 hours, then the mixture is washed with NaHCO$_3$ solution, dried, evaporated and 2-p-ethoxyphenyl-5-pentyltetrahydropyran is obtained.

The following can be obtained analogously:
2-m-Fluorophenyl-5-pentyl-tetrahydropyran
2-(2,3-Difluorophenyl)-5-pentyl-tetrahydropyran
2-p-Methoxyphenyl-5-propyl-tetrahydropyran
2-p-Methoxyphenyl-5-butyl-tetrahydropyran
2-p-Methoxyphenyl-5-pentyl-tetrahydropyran
2-p-Methoxyphenyl-5-hexyl-tetrahydropyran
2-p-Methoxyphenyl-5-heptyl-tetrahydropyran
2-p-Methoxyphenyl-5-octyl-tetrahydropyran
2-p-Ethoxyphenyl-5-propyl-tetrahydropyran
2-p-Ethoxyphenyl-5-butyl-tetrahydropyran
2-p-Ethoxyphenyl-5-hexyl-tetrahydropyran
2-p-Ethoxyphenyl-5-heptyl-tetrahydropyran
2-p-Ethoxyphenyl-5-octyl-tetrahydropyran
2-p-Propoxyphenyl-5-propyl-tetrahydropyran
2-p-Propoxyphenyl-5-butyl-tetrahydropyran
2-p-Propoxyphenyl-5-pentyl-tetrahydropyran
2-p-Propoxyphenyl-5-hexyl-tetrahydropyran
2-p-Propoxyphenyl-5-heptyl-tetrahydropyran
2-p-Propoxyphenyl-5-octyl-tetrahydropyran.

EXAMPLE 4

In analogy to Example 3, 2-propyl-5-phenyltetrahydropyran is obtained from 2-phenyl-1,5-octanediol [obtainable by reaction of butyronitrile with 2-tetrahydropyranyloxyethyl magnesium bromide to give 1-tetrahydropyranyloxy-3-hexanone, ether cleavage, ketalization and reaction with PBr$_3$ to give 1-bromo-3-hexanone ethylene ketal, reaction with diethyl phenylmalonate to give diethyl phenyl(3-oxohexyl)malonate, hydrolysis and decarboxylation to give 2-phenyl-5-oxooctanoic acid and reduction with LiAlH$_4$].

The following can be obtained analogously:
2-Butyl-5-phenyl-tetrahydropyran
2-Pentyl-5-phenyl-tetrahydropyran
2-Hexyl-5-phenyl-tetrahydropyran
2-Heptyl-5-phenyl-tetrahydropyran
2-Octyl-5-phenyl-tetrahydropyran
2-Propyl-5-p-methoxyphenyl-tetrahydropyran
2-Butyl-5-p-methoxyphenyl-tetrahydropyran
2-Pentyl-5-p-methoxyphenyl-tetrahydropyran
2-Hexyl-5-p-methoxyphenyl-tetrahydropyran
2-Heptyl-5-p-methoxyphenyl-tetrahydropyran
2-Octyl-5-p-methoxyphenyl-tetrahydropyran
2-Propyl-5-p-ethoxyphenyl-tetrahydropyran
2-Butyl-5-p-ethoxyphenyl-tetrahydropyran
2-Pentyl-5-p-ethoxyphenyl-tetrahydropyran
2-Hexyl-5-p-ethoxyphenyl-tetrahydropyran
2-Heptyl-5-p-ethoxyphenyl-tetrahydropyran
2-Octyl-5-p-ethoxyphenyl-tetrahydropyran
2-Propyl-5-p-tolyl-tetrahydropyran
2-Butyl-5-p-tolyl-tetrahydropyran
2-Pentyl-5-p-tolyl-tetrahydropyran
2-Hexyl-5-p-tolyl-tetrahydropyran
2-Heptyl-5-p-tolyl-tetrahydropyran
2-Octyl-5-p-tolyl-tetrahydropyran
2-Propyl-5-p-ethylphenyl-tetrahydropyran
2-Butyl-5-p-ethylphenyl-tetrahydropyran
2-Pentyl-5-p-ethylphenyl-tetrahydropyran
2-Hexyl-5-p-ethylphenyl-tetrahydropyran
2-Heptyl-5-p-ethylphenyl-tetrahydropyran
2-Octyl-5-p-ethylphenyl-tetrahydropyran
2-Propyl-5-p-propylphenyl-tetrahydropyran
2-Butyl-5-p-propylphenyl-tetrahydropyran
2-Pentyl-5-p-propylphenyl-tetrahydropyran
2-Hexyl-5-p-propylphenyl-tetrahydropyran
2-Heptyl-5-p-propylphenyl-tetrahydropyran
2-Octyl-5-p-propylphenyl-tetrahydropyran
2-Propyl-5-p-butylphenyl-tetrahydropyran
2-Butyl-5-p-butylphenyl-tetrahydropyran
2-Pentyl-5-p-butylphenyl-tetrahydropyran
2-Hexyl-5-p-butylphenyl-tetrahydropyran
2-Heptyl-5-p-butylphenyl tetrahydropyran
2-Octyl-5-p-butylphenyl-tetrahydropyran
2-Propyl-5-p-pentylphenyl-tetrahydropyran
2-Butyl-5-p-pentylphenyl-tetrahydropyran
2-Pentyl-5-p-pentylphenyl-tetrahydropyran
2-Hexyl-5-p-pentylphenyl-tetrahydropyran
2-Heptyl-5-p-pentylphenyl-tetrahydropyran
2-Octyl-5-p-pentylphenyl-tetrahydropyran
2-Propyl-5-p-hexylphenyl-tetrahydropyran
2-Butyl-5-p-hexylphenyl-tetrahydropyran
2-Pentyl-5-p-hexylphenyl-tetrahydropyran
2-Hexyl-5-p-hexylphenyl-tetrahydropyran
2-Heptyl-5-p-hexylphenyl-tetrahydropyran
2-Octyl-5-p-hexylphenyl-tetrahydropyran
2-Propyl-5-p-heptylphenyl-tetrahydropyran
2-Butyl-5-p-heptylphenyl-tetrahydropyran
2-Pentyl-5-p-heptylphenyl-tetrahydropyran
2-Hexyl-5-p-heptylphenyl-tetrahydropyran
2-Heptyl-5-p-heptylphenyl-tetrahydropyran
2-Octyl-5-p-heptylphenyl-tetrahydropyran
2-Propyl-5-p-octylphenyl-tetrahydropyran
2-Butyl-5-p-octylphenyl-tetrahydropyran
2-Pentyl-5-p-octylphenyl-tetrahydropyran
2-Hexyl-5-p-octylphenyl-tetrahydropyran
2-Heptyl-5-p-octylphenyl-tetrahydropyran
2-Octyl-5-p-octylphenyl-tetrahydropyran
2-Propyl-5-p-fluorophenyl-tetrahydropyran
2-Butyl-5-p-fluorophenyl-tetrahydropyran 2-Pentyl-5-p-fluorophenyl-tetrahydropyran
2-Hexyl-5-p-fluorophenyl-tetrahydropyran
2-Heptyl-5-p-fluorophenyl-tetrahydropyran
2-Octyl-5-p-fluorophenyl-tetrahydropyran
2-Propyl-5-p-chlorophenyl-tetrahydropyran
2-Butyl-5-p-chlorophenyl-tetrahydropyran
2-Pentyl-5-p-chlorophenyl-tetrahydropyran
2-Hexyl-5-p-chlorophenyl-tetrahydropyran
2-Heptyl-5-p-chlorophenyl-tetrahydropyran
2-Octyl-5-p-chlorophenyl-tetrahydropyran
2-Propyl-5-p-bromophenyl-tetrahydropyran
2-Butyl-5-p-bromophenyl-tetrahydropyran
2-Pentyl-5-p-bromophenyl-tetrahydropyran
2-Hexyl-5-p-bromophenyl-tetrahydropyran
2-Heptyl-5-p-bromophenyl-tetrahydropyran
2-Octyl-5-p-bromophenyl-tetrahydropyran
2-Propyl-5-(4-biphenylyl)-tetrahydropyran
2-Butyl-5-(4-biphenylyl)-tetrahydropyran
2-Pentyl-5-(4-biphenylyl)-tetrahydropyran
2-Hexyl-5-(4-biphenylyl)-tetrahydropyran
2-Heptyl-5-(4-biphenylyl)-tetrahydropyran
2-Octyl-5-(4-biphenylyl)-tetrahydropyran.

EXAMPLE 5

3.16 g of crude 2-hexyl-2-(3-hydroxy-3-p-pentylphenylpropyl)malonic acid [oily; obtainable by Friedel-Crafts reaction of pentylbenzene with 3-bromopropionyl chloride to give p-pentyl-ω-bromopropiophenone, reaction with diethyl 2-hexylmalonate to give diethyl 2-hexyl-2-(3-oxo-3-p-pentylphenylpropyl)malonate, $NaBH_4$ reduction to give diethyl 2-hexyl-2-(3-hydroxy-3-p-pentylphenylpropyl)malonate and hydrolysis are heated at 210° for 30 minutes. The compounds, which are formed as intermediates by cyclization and decarboxylation respectively, 2-oxo-3-hexyl-6-p-pentylphenyltetrahydropyran-3-carboxylic acid and 2-(3-hydroxy-3-p-pentylphenylpropyl)octanoic acid, are not isolated. After usual work-up, 2-oxo-3-hexyl-6-p-pentylphenyltetrahydropyran, m.p. 101°–102°, is obtained.

The following can be obtained analogously:
2-Oxo-3-propyl-6-phenyl-tetrahydropyran
2-Oxo-3-butyl-6-phenyl-tetrahydropyran
2-Oxo-3-pentyl-6-phenyl-tetrahydropyran
2-Oxo-3-hexyl-6-phenyl-tetrahydropyran
2-Oxo-3-heptyl-6-phenyl-tetrahydropyran
2-Oxo-3-octyl-6-phenyl-tetrahydropyran
2-Oxo-3-propyl-6-p-tolyl-tetrahydropyran
2-Oxo-3-butyl-6-p-tolyl-tetrahydropyran
2-Oxo-3-pentyl-6-p-tolyl-tetrahydropyran
2-Oxo-3-hexyl-6-p-tolyl-tetrahydropyran
2-Oxo-3-heptyl-6-p-tolyl-tetrahydropyran
2-Oxo-3-octyl-6-p-tolyl-tetrahydropyran
2-Oxo-3-propyl-6-p-ethylphenyl-tetrahydropyran
2-Oxo-3-butyl-6-p-ethylphenyl-tetrahydropyran
2-Oxo-3-pentyl-6-p-ethylphenyl-tetrahydropyran
2-Oxo-3-hexyl-6-p-ethylphenyl-tetrahydropyran
2-Oxo-3-heptyl-6-p-ethylphenyl-tetrahydropyran
2-Oxo-3-octyl-6-p-ethylphenyl-tetrahydropyran
2-Oxo-3-propyl-6-p-propylphenyl-tetrahydropyran
2-Oxo-3-butyl-6-p-propylphenyl-tetrahydropyran
2-Oxo-3-pentyl-6-p-propylphenyl-tetrahydropyran
2-Oxo-3-hexyl-6-p-propylphenyl-tetrahydropyran
2-Oxo-3-heptyl-6-p-propylphenyl-tetrahydropyran
2-Oxo-3-octyl-6-p-propylphenyl-tetrahydropyran
2-Oxo-3-propyl-6-p-butylphenyl-tetrahydropyran
2-Oxo-3-butyl-6-p-butylphenyl-tetrahydropyran
2-Oxo-3-pentyl-6-p-butylphenyl-tetrahydropyran
2-Oxo-3-hexyl-6-p-butylphenyl-tetrahydropyran
2-Oxo-3-heptyl-6-p-butylphenyl-tetrahydropyran
2-Oxo-3-octyl-6-p-butylphenyl-tetrahydropyran
2-Oxo-3-propyl-6-p-pentylphenyl-tetrahydropyran
2-Oxo-3-butyl-6-p-pentylphenyl-tetrahydropyran
2-Oxo-3-pentyl-6-p-pentylphenyl-tetrahydropyran
2-Oxo-3-heptyl-6-p-pentylphenyl-tetrahydropyran, m.p. 91°
2-Oxo-3-octyl-6-p-pentylphenyl-tetrahydropyran
2-Oxo-3-propyl-6-p-hexylphenyl-tetrahydropyran
2-Oxo-3-butyl-6-p-hexylphenyl-tetrahydropyran
2-Oxo-3-pentyl-6-p-hexylphenyl-tetrahydropyran
2-Oxo-3-hexyl-6-p-hexylphenyl-tetrahydropyran
2-Oxo-3-heptyl-6-p-hexylphenyl-tetrahydropyran
2-Oxo-3-octyl-6-p-hexylphenyl-tetrahydropyran
2-Oxo-3-propyl-6-p-heptylphenyl-tetrahydropyran
2-Oxo-3-butyl-6-p-heptylphenyl-tetrahydropyran
2-Oxo-3-pentyl-6-p-heptylphenyl-tetrahydropyran
2-Oxo-3-hexyl-6-p-heptylphenyl-tetrahydropyran
2-Oxo-3-heptyl-6-p-heptylphenyl-tetrahydropyran
2-Oxo-3-octyl-6-p-heptylphenyl-tetrahydropyran
2-Oxo-3-propyl-6-p-octylphenyl-tetrahydropyran
2-Oxo-3-butyl-6-p-octylphenyl-tetrahydropyran
2-Oxo-3-pentyl-6-p-octylphenyl-tetrahydropyran
2-Oxo-3-hexyl-6-p-octylphenyl-tetrahydropyran
2-Oxo-3-heptyl-6-p-octylphenyl-tetrahydropyran
2-Oxo-3-octyl-6-p-octylphenyl-tetrahydropyran
2-Oxo-3-propyl-6-p-methoxyphenyl-tetrahydropyran
2-Oxo-3-butyl-6-p-methoxyphenyl-tetrahydropyran
2-Oxo-3-pentyl-6-p-methoxyphenyl-tetrahydropyran
2-Oxo-3-hexyl-6-p-methoxyphenyl-tetrahydropyran
2-Oxo-3-heptyl-6-p-methoxyphenyl-tetrahydropyran
2-Oxo-3-octyl-6-p-methoxyphenyl-tetrahydropyran
2-Oxo-3-propyl-6-p-ethoxyphenyl-tetrahydropyran
2-Oxo-3-butyl-6-p-ethoxyphenyl-tetrahydropyran
2-Oxo-3-pentyl-6-p-ethoxyphenyl-tetrahydropyran
2-Oxo-3-hexyl-6-p-ethoxyphenyl-tetrahydropyran
2-Oxo-3-heptyl-6-p-ethoxyphenyl-tetrahydropyran
2-Oxo-3-octyl-6-p-ethoxyphenyl-tetrahydropyran

EXAMPLE 6

A mixture of 2.34 g of 2-phenyl-5-oxooctanoic acid, 0.3 g of $NaBH_4$, 0.5 g of NaOH and 25 ml of methanol is boiled for 5 hours and worked up as usual. 2-Phenyl-5-hydroxyoctanoic acid is formed as an intermediate but is not isolated. 2-Oxo-3-phenyl-6-propyltetrahydropyran is obtained.

The following can be obtained analogously:
2-Oxo-3-phenyl-6-butyl-tetrahydropyran
2-Oxo-3-phenyl-6-pentyl-tetrahydropyran
2-Oxo-3-phenyl-6-hexyl-tetrahydropyran
2-Oxo-3-phenyl-6-heptyl-tetrahydropyran
2-Oxo-3-phenyl-6-octyl-tetrahydropyran
2-Oxo-3-p-tolyl-6-propyl-tetrahydropyran
2-Oxo-3-p-tolyl-6-butyl-tetrahydropyran
2-Oxo-3-p-tolyl-6-pentyl-tetrahydropyran
2-Oxo-3-p-tolyl-6-hexyl-tetrahydropyran
2-Oxo-3-p-tolyl-6-heptyl-tetrahydropyran
2-Oxo-3-p-tolyl-6-octyl-tetrahydropyran
2-Oxo-3-p-ethylphenyl-propyl-tetrahydropyran
2-Oxo-3-p-ethylphenyl-butyl-tetrahydropyran
2-Oxo-3-p-ethylphenyl-pentyl-tetrahydropyran
2-Oxo-3-p-ethylphenyl-hexyl-tetrahydropyran
2-Oxo-3-p-ethylphenyl-heptyl-tetrahydropyran
2-Oxo-3-p-ethylphenyl-octyl-tetrahydropyran
2-Oxo-3-p-propylphenyl-propyl-tetrahydropyran
2-Oxo-3-p-propylphenyl-butyl-tetrahydropyran
2-Oxo-3-p-propylphenyl-pentyl-tetrahydropyran
2-Oxo-3-p-propylphenyl-hexyl-tetrahydropyran 2-Oxo-3-p-propylphenyl-heptyl-tetrahydropyran
2-Oxo-3-p-propylphenyl-octyl-tetrahydropyran
2-Oxo-3-p-butylphenyl-propyl-tetrahydropyran
2-Oxo-3-p-butylphenyl-butyl-tetrahydropyran
2-Oxo-3-p-butylphenyl-pentyl-tetrahydropyran
2-Oxo-3-p-butylphenyl-hexyl-tetrahydropyran
2-Oxo-3-p-butylphenyl-heptyl-tetrahydropyran
2-Oxo-3-p-butylphenyl-octyl-tetrahydropyran
2-Oxo-3-p-pentylphenyl-propyl-tetrahydropyran
2-Oxo-3-p-pentylphenyl-butyl-tetrahydropyran
2-Oxo-3-p-pentylphenyl-pentyl-tetrahydropyran
2-Oxo-3-p-pentylphenyl-hexyl-tetrahydropyran
2-Oxo-3-p-pentylphenyl-heptyl-tetrahydropyan
2-Oxo-3-p-pentylphenyl-octyl-tetrahydropyran
2-Oxo-3-p-hexylphenyl-propyl-tetrahydropyran
2-Oxo-3-p-hexylphenyl-butyl-tetrahydropyran
2-Oxo-3-p-hexylphenyl-pentyl-tetrahydropyran
2-Oxo-3-p-hexylphenyl-hexyl-tetrahydropyran
2-Oxo-3-p-hexylphenyl-heptyl-tetrahydropyran
2-Oxo-3-p-hexylphenyl-octyl-tetrahydropyran
2-Oxo-3-p-heptylphenyl-propyl-tetrahydropyran
2-Oxo-3-p-heptylphenyl-butyl-tetrahydropyran
2-Oxo-3-p-heptylphenyl-pentyl-tetrahydropyran
2-Oxo-3-p-heptylphenyl-hexyl-tetrahydropyran
2-Oxo-3-p-heptylphenyl-heptyl-tetrahydropyran
2-Oxo-3-p-heptylphenyl-octyl-tetrahydropyran
2-Oxo-3-p-octylphenyl-6-propyl-tetrahydropyran
2-Oxo-3-p-octylphenyl-6-butyl-tetrahydropyran
2-Oxo-3-p-octylphenyl-6-pentyl-tetrahydropyran
2-Oxo-3-p-octylphenyl-6-hexyl-tetrahydropyran
2-Oxo-3-p-octylphenyl-6-heptyl-tetrahydropyran
2-Oxo-3-p-octylphenyl-6-octyl-tetrahydropyran
2-Oxo-3-p-methoxyphenyl-6-propyl-tetrahydropyran
2-Oxo-3-p-methoxyphenyl-6-butyl-tetrahydropyran
2-Oxo-3-p-methoxyphenyl-6-pentyl-tetrahydropyran
2-Oxo-3-p-methoxyphenyl-6-hexyl-tetrahydropyran
2-Oxo-3-p-methoxyphenyl-6-heptyl-tetrahydropyran
2-Oxo-3-p-methoxyphenyl-6-octyl-tetrahydropyran
2-Oxo-3-p-ethoxyphenyl-6-propyl-tetrahydropyran
2-Oxo-3-p-ethoxyphenyl-6-butyl-tetrahydropyran
2-Oxo-3-p-ethoxyphenyl-6-pentyl-tetrahydropyran
2-Oxo-3-p-ethoxyphenyl-6-hexyl-tetrahydropyran
2-Oxo-3-p-ethoxyphenyl-6-heptyl-tetrahydropyran
2-Oxo-3-p-ethoxyphenyl-6-octyl-tetrahydropyran.

EXAMPLE 7

A solution of 4.04 g of 4-hydroxymethyl-1-phenyl-1-nonanol mono-p-toluenesulfonate (obtainable by Friedel-Crafts reaction of 2-pentylglutaric anhydride with benzene to give 4-benzoyl-2-pentylbutyric acid, LiAlH$_4$ reduction to give 4-hydroxymethyl-1-phenyl-1-nonanol and reaction with p-toluenesulfonyl chloride in triethylamine/CH$_2$Cl$_2$) in 100 ml of phosphoric hexamethyltriamide is heated at 80° for 24 hours. The solution is evaporated, worked up as usual and 2-phenyl-5-pentyltetrahydropyran is obtained as an oily mixture of isomers. Isomerisation of 2 g of the mixture by heating with 0.19 g of K tert.butylate in 20 ml of dimethyl sulfoxide at 80° for two hours leads to trans-2-phenyl-5-pentyltetrahydropyran.

The following can be obtained analogously:
2-Phenyl-5-propyl-tetrahydropyran
2-Phenyl-5-butyl-tetrahydropyran
2-Phenyl-5-hexyl-tetrahydropyran
2-Phenyl-5-heptyl-tetrahydropyran
2-Phenyl-5-octyl-tetrahydropyran
2-p-Tolyl-5-propyl-tetrahydropyran
2-p-Tolyl-5-butyl-tetrahydropyran
2-p-Tolyl-5-pentyl-tetrahydropyran
2-p-Tolyl-5-hexyl-tetrahydropyran
2-p-Tolyl-5-heptyl-tetrahydropyran
2-p-Tolyl-5-octyl-tetrahydropyran
2-p-Ethylphenyl-5-propyl-tetrahydropyran
2-p-Ethylphenyl-5-butyl-tetrahydropyran
2-p-Ethylphenyl-5-pentyl-tetrahydropyran
2-p-Ethylphenyl-5-hexyl-tetrahydropyran
2-p-Ethylphenyl-5-heptyl-tetrahydropyran
2-p-Ethylphenyl-5-octyl-tetrahydropyran
2-p-Propylphenyl-5-propyl-tetrahydropyran
2-p-Propylphenyl-5-butyl-tetrahydropyran
2-p-Propylphenyl-5-pentyl-tetrahydropyran
2-p-Propylphenyl-5-hexyl-tetrahydropyran
2-p-Propylphenyl-5-heptyl-tetrahydropyran
2-p-Propylphenyl-5-octyl-tetrahydropyran
2-p-Butylphenyl-5-propyl-tetrahydropyran
2-p-Butylphenyl-5-butyl-tetrahydropyran
2-p-Butylphenyl-5-pentyl-tetrahydropyran
2-p-Butylphenyl-5-hexyl-tetrahydropyran
2-p-Butylphenyl-5-heptyl-tetrahydropyran
2-p-Butylphenyl-5-octyl-tetrahydropyran
2-p-Pentylphenyl-5-propyl-tetrahydropyran
2-p-Pentylphenyl-5-butyl-tetrahydropyran
2-p-Pentylphenyl-5-pentyl-tetrahydropyran
2-p-Pentylphenyl-5-hexyl-tetrahydropyran
2-p-Pentylphenyl-5-heptyl-tetrahydropyran, Boiling point 210°–215°/0.01 mbar
2-p-Pentylphenyl-5-octyl-tetrahydropyran
2-p-Hexylphenyl-5-propyl-tetrahydropyran
2-p-Hexylphenyl-5-butyl-tetrahydropyran
2-p-Hexylphenyl-5-pentyl-tetrahydropyran
2-p-Hexylphenyl-5-hexyl-tetrahydropyran
2-p-Hexylphenyl-5-heptyl-tetrahydropyran
2-p-Hexylphenyl-5-octyl-tetrahydropyran
2-p-Heptylphenyl-5-propyl-tetrahydropyran
2-p-Heptylphenyl-5-butyl-tetrahydropyran
2-p-Heptylphenyl-5-pentyl-tetrahydropyran
2-p-Heptylphenyl-5-hexyl-tetrahydropyran
2-p-Heptylphenyl-5-heptyl-tetrahydropyran
2-p-Heptylphenyl-5-octyl-tetrahydropyran
2-p-Octylphenyl-5-propyl-tetrahydropyran
2-p-Octylphenyl-5-butyl-tetrahydropyran
2-p-Octylphenyl-5-pentyl-tetrahydropyran
2-p-Octylphenyl-5-hexyl-tetrahydropyran
2-p-Octylphenyl-5-heptyl-tetrahydropyran
2-p-Octylphenyl-5-octyl-tetrahydropyran
2-(4-Biphenylyl)-5-propyl-tetrahydropyran
2-(4-Biphenylyl)-5-butyl-tetrahydropyran
2-(4-Biphenylyl)-5-pentyl-tetrahydropyran
2-(4-Biphenylyl)-5-hexyl-tetrahydropyran
2-(4-Biphenylyl)-5-heptyl-tetrahydropyran
2-(4-Biphenylyl)-5-octyl-tetrahydropyran
2-(4'-Methyl-4-biphenylyl)-5-propyl-tetrahydropyran
2-(4'-Methyl-4-biphenylyl)-5-butyl-tetrahydropyran
2-(4'-Methyl-4-biphenylyl)-5-pentyl-tetrahydropyran
2-(4'-Methyl-4-biphenylyl)5-hexyl-tetrahydropyran
2-(4'-Methyl-4-biphenylyl)-5-heptyl-tetrahydropyran
2-(4'-Methyl-4-biphenylyl)-5-octyl-tetrahydropyran
2-(4'-Ethyl-4-biphenylyl)-5-propyl-tetrahydropyran
2-(4'-Ethyl-4-biphenylyl)-5-butyl-tetrahydropyran
2-(4'-Ethyl-4-biphenylyl)-5-pentyl-tetrahydropyran
2-(4'-Ethyl-4-biphenylyl)-5-hexyl-tetrahydropyran
2-(4'-Ethyl-4-biphenylyl)-5-heptyl-tetrahydropyran
2-(4'-Ethyl-4-biphenylyl)-5-octyl-tetrahydropyran
2-(4'-Propyl-4-biphenylyl)-5-propyl-tetrahydropyran
2-(4'-Propyl-4-biphenylyl)-5-butyl-tetrahydropyran
2-(4'-Propyl-4-biphenylyl)-5-pentyl-tetrahydropyran 2-(4'-Propyl-4-biphenylyl)-5-hexyl-tetrahydropyran
2-(4'-Propyl-4-biphenylyl)-5-heptyl-tetrahydropyran
2-(4'-Propyl-4-biphenylyl)-5-octyl-tetrahydropyran
2-(4'-Butyl-4-biphenylyl)-5-propyl-tetrahydropyran
2-(4'-Butyl-4-biphenylyl)-5-butyl-tetrahydropyran
2-(4'-Butyl-4-biphenylyl)-5-pentyl-tetrahydropyran
2-(4'-Butyl-4-biphenylyl)-5-hexyl-tetrahydropyran
2-(4'-Butyl-4-biphenylyl)-5-heptyl-tetrahydropyran
2-(4'-Butyl-4-biphenylyl)-5-octyl-tetrahydropyran
2-(4'-Pentyl-4-biphenylyl)-5-propyl-tetrahydropyran
2-(4'-Pentyl-4-biphenylyl)-5-butyl-tetrahydropyran
2-(4'-Pentyl-4-biphenylyl)-5-pentyl-tetrahydropyran
2-(4'-Pentyl-4-biphenylyl)-5-hexyl-tetrahydropyran
2-(4'-Pentyl-4-biphenylyl)-5-heptyl-tetrahyropyran
2-(4'-Pentyl-4-biphenylyl)-5-octyl-tetrahydropyran
2-(4'-Hexyl-4-biphenylyl)-5-propyl-tetrahydropyran
2-(4'-Hexyl-4-biphenylyl)-5-butyl-tetrahydropyran
2-(4'-Hexyl-4-biphenylyl)-5-pentyl-tetrahydropyran
2-(4'-Hexyl-4-biphenylyl)-5-hexyl-tetrahydropyran
2-(4'-Hexyl-4-biphenylyl)-5-heptyl-tetrahydropyran
2-(4'-Hexyl-4-biphenylyl)-5-octyl-tetrahyropyran
2-(4'-Heptyl-4-biphenylyl)-5-propyl-tetrahydropyran
2-(4'-Heptyl-4-biphenylyl)-5-butyl-tetrahydropyran
2-(4'-Heptyl-4-biphenylyl)-5-pentyl-tetrahydropyran
2-(4'-Heptyl-4-biphenylyl)-5-hexyl-tetrahydropyran
2-(4'-Heptyl-4-biphenylyl)-5-heptyl-tetrahydropyran
2-(4'-Heptyl-4-biphenylyl)-5-octyl-tetrahydropyran
2-(4'-Octyl-4-biphenylyl)-5-propyl-tetrahydropyran
2-(4'-Octyl-4-biphenylyl)-5-butyl-tetrahydropyran
2-(4'-Octyl-4-biphenylyl)-5-pentyl-tetrahydropyran
2-(4'-Octyl-4-biphenylyl)-5-hexyl-tetrahydropyran
2-(4'-Octyl-4-biphenylyl)-5-heptyl-tetrahydropyran
2-(4'-Octyl-4-biphenylyl)-5-octyl-tetrahydropyran
2-(4'-Methoxy-4-biphenylyl)-5-propyl-tetrahydropyran
2-(4'-Methoxy-4-biphenylyl)-5-butyl-tetrahydropyran
2-(4'-Methoxy-4-biphenylyl)-5-pentyl-tetrahydropyran
2-(4'-Methoxy-4-biphenylyl)-5-hexyl-tetrahydropyran
2-(4'-Methoxy-4-biphenylyl)-5-heptyl-tetrahydropyran
2-(4'-Methoxy-4-biphenylyl)-5-octyl-tetrahydropyran
2-(4'-Ethoxy-4-biphenylyl)-5-propyl-tetrahydropyran
2-(4'-Ethoxy-4-biphenylyl)-5-butyl-tetrahydropyran
2-(4'-Ethoxy-4-biphenylyl)-5-pentyl-tetrahydropyran
2-(4'-Ethoxy-4-biphenylyl)-5-hexyl-tetrahydropyran
2-(4'-Ethoxy-4-biphenylyl)-5-heptyl-tetrahydropyran
2-(4'-Ethoxy-4-biphenylyl)-5-octyl-tetrahydropyran
2-(4'-(trans-4-Propylcyclohexyl)-4-biphenylyl)-5-propyltetrahydropyran
2-(4'-(trans-4-Propylcyclohexyl)-4-biphenylyl)-5-butyltetrahydropyran
2-(4'-(trans-4-Propylcyclohexyl)-4-biphenylyl)-5-pentyl-tetrahydropyran
2-(4'-(trans-4-Propylcyclohexyl)-4-biphenylyl)-5-hexyl-tetrahydropyran
2-(4'-(trans-4-Propylcyclohexyl)-4-biphenylyl)-5-heptyl-tetrahydropyran
2-(4'-(trans-4-Propylcyclohexyl)-4-biphenylyl)-5-octyl-tetrahydropyran
2-(4'-(trans-4-Butylcyclohexyl)-4-biphenylyl)-5-propyl-tetrahydropyran
2-(4'-(trans-4-Butylcyclohexyl)-4-biphenylyl)-5-butyl-tetrahydropyran
2-(4'-(trans-4-Butylcyclohexyl)-4-biphenylyl)-5-pentyl-tetrahydropyran
2-(4'-(trans-4-Butylcyclohexyl)-4-biphenylyl)-5-hexyl-tetrahydropyran
2-(4'-(trans-4-Butylcyclohexyl)-4-biphenylyl)-5-heptyl-tetrahydropyran
2-(4'-(trans-4-Butylcyclohexyl)-4-biphenylyl)-5-octyl-tetrahydropyran
2-(4'-(trans-4-Pentylcyclohexyl)-4-biphenylyl)-5-propyl-tetrahydropyran
2-(4'-(trans-4-Pentylcyclohexyl)-4-biphenylyl)-5-butyl-tetrahydropyran
2-(4'-(trans-4-Pentylcyclohexyl)-4-biphenylyl)-5-pentyl-tetrahydropyran
2-(4'-(trans-4-Pentylcyclohexyl)-4-biphenylyl)-5-hexyl-tetrahydropyran
2-(4'-(trans-4-Pentylcyclohexyl)-4-biphenylyl)-5-heptyl-tetrahydropyran
2-(4'-(trans-4-Pentylcyclohexyl)-4-biphenylyl)-5-octyl-tetrahydropyran
2-(4'-(trans-4-Hexylcyclohexyl)-4-biphenylyl)-5-propyl-tetrahydropyran
2-(4'-(trans-4-Hexylcyclohexyl)-4-biphenylyl)-5-butyl-tetrahydropyran
2-(4'-(trans-4-Hexylcyclohexyl)-4-biphenylyl)-5-pentyl-tetrahydropyran
2-(4'-(trans-4-Hexylcyclohexyl)-4-biphenylyl)-5-hexyl-tetrahydropyran
2-(4'-(trans-4-Hexylcyclohexyl)-4-biphenylyl)-5-heptyl-tetrahydropyran
2-(4'-(trans-4-Hexylcyclohexyl)-4-biphenylyl)-5-octyl-tetrahydropyran
2-(4'-(trans-4-Heptylcyclohexyl)-4-biphenylyl)-5-propyl-tetrahydropyran
2-(4'-(trans-4-Heptylcyclohexyl)-4-biphenylyl)-5-butyl-tetrahydropyran
2-(4'-(trans-4-Heptylcyclohexyl)-4-biphenylyl)-5-pentyl-tetrahydropyran
2-(4'-(trans-4-Heptylcyclohexyl)-4-biphenylyl)-5-hexyl-tetrahydropyran
2-(4'-(trans-4-Heptylcyclohexyl)-4-biphenylyl)-5-heptyl-tetrahydropyran
2-(4'-(trans-4-Heptylcyclohexyl)-4-biphenylyl)-5-octyl-tetrahydropyran.

EXAMPLE 8

24.7 g of 2-p-aminophenyl-5-pentyltetrahydropyran (obtainable by, for example, nitration of 2-phenyl-5-pentyltetrahydropyran followed by hydrogenation of the resulting 2-p-nitrophenyl-5-pentyltetrahydropyran) are dissolved in a mixture of 25 ml of concentrated hydrochloric acid and 75 ml of water, and diazotized at 3°–6° with a solution of 8 g of $NaNO_2$ in 15 ml of water. The diazonium salt solution thus obtained is added within 15 minutes to a solution of $Cu_2(CN)_2$ (prepared by heating 25 g of copper sulfate with 28 g of KCN in 100 ml of water) which is heated at 60°–70°. Heating is continued for 20 minutes at 100°, the mixture is cooled and, after usual work-up, 2-p-cyanophenyl-5-pentyltetrahydropyran is obtained.

The following can be obtained analogously:
2-p-Cyanophenyl-5-methyl-tetrahydropyran
2-p-Cyanophenyl-5-ethyl-tetrahydropyran
2-p-Cyanophenyl-5-propyl-tetrahydropyran
2-p-Cyanophenyl-5-butyl-tetrahydropyran
2-p-Cyanophenyl-5-hexyl-tetrahydropyran
2-p-Cyanophenyl-5-heptyl-tetrahydropyran
2-p-Cyanophenyl-5-octyl-tetrahydropyran
2-p-Cyanophenyl-5-nonyl-tetrahydropyran
2-p-Cyanophenyl-5-decyl-tetrahydropyran
2-Oxo-3-propyl-6-p-cyanophenyl-tetrahydropyran
2-Oxo-3-butyl-6-p-cyanophenyl-tetrahydropyran
2-Oxo-3-pentyl-6-p-cyanophenyl-tetrahydropyran
2-Oxo-3-hexyl-6-p-cyanophenyl-tetrahydropyran 2-Oxo-3-heptyl-6-p-cyanophenyl-tetrahydropyran
2-Oxo-3-octyl-6-p-cyanophenyl-tetrahydropyran
2-(4'-Cyano-4-biphenylyl)-5-propyl-tetrahydropyran
2-(4'-Cyano-4-biphenylyl)-5-butyl-tetrahydropyran
2-(4'-Cyano-4-biphenylyl)-5-pentyl-tetrahydropyran
2-(4'-Cyano-4-biphenylyl)-5-hexyl-tetrahydropyran
2-(4'-Cyano-4-biphenylyl)-5-heptyl-tetrahydropyran
1-(4'-Cyano-4-biphenylyl)-5-octyl-tetrahydropyran
2-Methyl-5-p-cyanophenyl-tetrahydropyran
2-Ethyl-5-p-cyanophenyl-tetrahydropyran
2-Propyl-5-p-cyanophenyl-tetrahydropyran
2-Butyl-5-p-cyanophenyl-tetrahydropyran
2-Pentyl-5-p-cyanophenyl-tetrahydropyran
2-Hexyl-5-p-cyanophenyl-tetrahydropyran
2-Heptyl-5-p-cyanophenyl-tetrahydropyran
2-Octyl-5-p-cyanophenyl-tetrahydropyran
2-Nonyl-5-p-cyanophenyl-tetrahydropyran
2-Decyl-5-p-cyanophenyl-tetrahydropyran
2-Oxo-3-p-cyanophenyl-6-propyl-tetrahydropyran
2-Oxo-3-p-cyanophenyl-6-butyl-tetrahydropyran
2-Oxo-3-p-cyanophenyl-6-pentyl-tetrahydropyran
2-Oxo-3-p-cyanophenyl-6-hexyl-tetrahydropyran
2-Oxo-3-p-cyanophenyl-6-heptyl-tetrahydropyran
2-Oxo-3-p-cyanophenyl-6-octyl-tetrahydropyran
2-Propyl-5-(4'-cyano-5-biphenylyl)-tetrahydropyran
2-Butyl-5-(4'-cyano-4-biphenylyl)-tetrahydropyran
2-Pentyl-5-(4'-cyano-4-biphenylyl)-tetrahydropyran
2-Hexyl-5-(4'-cyano-4-biphenylyl)-tetrahydropyran
2-Heptyl-5-(4-cyano-4-biphenylyl)-tetrahydropyran
2-Octyl-5-(4'-cyano-4-biphenylyl)-tetrahydropyran.

EXAMPLE 9

The reaction is carried out analogously to Example 8, but in place of the $Cu_2(CN)_2$ solution, a gently boiling solution of $Cu_2Cl_2$ (prepared from 25 g of copper sulfate and 25 g of NaCl in 100 ml of water with $SO_2$) is used, and 2-p-chlorophenyl-5-pentyl-tetrahydropyran is obtained.

The following can be obtained analogously:
2-p-chlorophenyl-5-propyl-tetrahydropyran
2-p-Chlorophenyl-5-butyl-tetrahydropyran
2-p-Chlorophenyl-5-hexyl-tetrahydropyran
2-p-Chlorophenyl-5-heptyl-tetrahydropyran
2-p-Chlorophenyl-5-octyl-tetrahydropyran
2-Oxo-3-propyl-6-p-chlorophenyl-tetrahydropyran
2-Oxo-3-butyl-6-p-chlorophenyl-tetrahydropyran
2-Oxo-3-pentyl-6-p-chlorophenyl-tetrahydropyran
2-Oxo-3-hexyl-6-p-chlorophenyl-tetrahydropyran
2-Oxo-3-heptyl-6-p-chlorophenyl-tetrahydropyran
2-Oxo-3-octyl-6-p-chlorophenyl-tetrahydropyran
2-(4'-Chloro-4-biphenylyl)-5-propyl-tetrahydropyran
2-(4'-Chloro-4-biphenylyl)-5-butyl-tetrahydropyran
2-(4'-Chloro-4-biphenylyl)-5-pentyl-tetrahydropyran
2-(4'-Chloro-4-biphenylyl)-5-hexyl-tetrahydropyran
2-(4'-Chloro-4-biphenylyl)-5-heptyl-tetrahydropyran
2-(4'-Chloro-4-biphenylyl)-5-octyl-tetrahydropyran
2-Propyl-5-p-chlorophenyl-tetrahydropyran
2-Butyl-5-p-chlorophenyl-tetrahydropyran
2-Pentyl-5-p-chlorophenyl-tetrahydropyran
2-Hexyl-5-p-chlorophenyl-tetrahydropyran
2-Heptyl-5-p-chlorophenyl-tetrahydropyran
2-Octyl-5-p-chlorophenyl-tetrahydropyran
2-Oxo-3-p-chlorophenyl-6-propyl-tetrahydropyran
2-Oxo-3-p-chlorophenyl-6-butyl-tetrahydropyran
2-Oxo-3-p-chlorophenyl-6-pentyl-tetrahydropyran
2-Oxo-3-p-chlorophenyl-6-hexyl-tetrahydropyran
2-Oxo-3-p-chlorophenyl-6-heptyl-tetrahydropyran
2-Oxo-3-p-chlorophenyl-6-octyl-tetrahydropyran
2-Propyl-5-(4'-chloro-4-biphenylyl)-tetrahydropyran
2-Butyl-5-(4'-chloro-4-biphenylyl)-tetrahydropyran
2-Pentyl-5-(4'-chloro-4-biphenylyl)-tetrahydropyran
2-Hexyl-5-(4'-chloro-4-biphenylyl)-tetrahydropyran
2-Heptyl-5-(4'-chloro-4-biphenylyl)-tetrahydropyran
2-Octyl-5-(4'-chloro-4-biphenylyl)-tetrahydropyran

EXAMPLE 10

The reaction is carried out analogously to Example 8, but in place of the $Cu_2(CN)_2$ solution, a boiling solution of $Cu_2Br_2$ (prepared from 25 g of copper sulfate, 8 g of copper powder, 52 g of KBr, 6.4 ml of concentrated $H_2SO_4$ and 400 ml of water by boiling for 3 hours, is used, and 2-p-bromophenyl-5-pentyltetrahydropyran is obtained.

The following can be obtained analogously:
2-p-Bromophenyl-5-propyl-tetrahydropyran
2-p-Bromophenyl-5-butyl-tetrahydropyran
2-p-Bromophenyl-5-hexyl-tetrahydropyran
2-p-Bromophenyl-5-heptyl-tetrahydropyran
2-p-Bromophenyl-5-octyl-tetrahydropyran
2-Oxo-3-propyl-6-p-bromophenyl-tetrahydropyran
2-Oxo-3-butyl-6-p-bromophenyl-tetrahydropyran
2-Oxo-3-pentyl-6-p-bromophenyl-tetrahydropyran
2-Oxo-3-hexyl-6-p-bromophenyl-tetrahydropyran
2-Oxo-3-heptyl-6-p-bromophenyl-tetrahydropyran
2-Oxo-3-octyl-6-p-bromophenyl-tetrahydropyran
2-(4'-Bromo-4-biphenylyl)-5-propyl-tetrahydropyran
2-(4'-Bromo-4-biphenylyl)-5-butyl-tetrahydropyran
2-(4'-Bromo-4-biphenylyl)-5-pentyl-tetrahydropyran
2-(4'-Bromo-4-biphenylyl)-5-hexyl-tetrahydropyran
2-(4'-Bromo-4-biphenylyl)-5-heptyl-tetrahydropyran
2-(4'-Bromo-4-biphenylyl)-5-octyl-tetrahydropyran
2-Propyl-5-p-bromophenyl-tetrahydropyran
2-Butyl-5-p-bromophenyl-tetrahydropyran
2-Pentyl-5-p-bromophenyl-tetrahydropyran
2-Hexyl-5-p-bromophenyl-tetrahydropyran
2-Heptyl-5-p-bromophenyl-tetrahydropyran
2-Octyl-5-p-bromophenyl-tetrahydropyran
2-Oxo-3-p-bromophenyl-6-propyl-tetrahydropyran
2-Oxo-3-p-bromophenyl-6-butyl-tetrahydropyran
2-Oxo-3-p-bromophenyl-6-pentyl-tetrahydropyran
2-Oxo-3-p-bromophenyl-6-hexyl-tetrahydropyran
2-Oxo-3-p-bromophenyl-6-heptyl-tetrahydropyran
2-Oxo-3-p-bromophenyl-6-octyl-tetrahydropyran
2-Propyl-5-(4'-bromo-4-biphenylyl)-tetrahydropyran
2-Butyl-5-(4'-bromo-4-biphenylyl)-tetrahydropyran
2-Pentyl-5-(4'-bromo-4-biphenylyl)-tetrahydropyran
2-Hexyl-5-(4'-bromo-4-biphenylyl)-tetrahydropyran
2-Heptyl-5-(4'-bromo-4-biphenylyl)-tetrahydropyran
2-Octyl-5-(4'-bromo-4-biphenylyl)-tetrahydropyran

EXAMPLE 11

24.7 g of 2-p-aminophenyl-5-pentyl-tetrahydropyran are dissolved in a mixture of 25 ml of concentrated hydrochloric acid and 75 ml of water, and diazotized at 3°–6° with a solution of 8 g of $NaNO_2$ in 15 ml of water. Then 24 g of 40% tetrafluoroboric acid are added, and the precipitated diazonium tetrafluoroborate is filtered off, washed with water and dried. The diazonium salt is heated to about 150°, and the residue is worked up as usual. 2-p-Fluorophenyl-5-pentyl-tetrahydropyran is obtained.

The following are obtained analogously:
2-p-Fluorophenyl-5-propyl-tetrahydropyran
2-p-Fluorophenyl-5-butyl-tetrahydropyran
2-p-Fluorophenyl-5-hexyl-tetrahydropyran
2-p-Fluorophenyl-5-heptyl-tetrahydropyran 2-p-Fluorophenyl-5-octyl-tetrahydropyran
2-Oxo-3-propyl-6-p-fluorophenyl-tetrahydropyran
2-Oxo-3-butyl-6-p-fluorophenyl-tetrahydropyran
2-Oxo-3-pentyl-6-p-fluorophenyl-tetrahydropyran
2-Oxo-3-hexyl-6-p-fluorophenyl-tetrahydropyran
2-Oxo-3-heptyl-6-p-fluorophenyl-tetrahydropyran
2-Oxo-3-octyl-6-p-fluorophenyl-tetrahydropyran
2-(4'-fluoro-4-biphenylyl)-5-propyl-tetrahydropyran
2-(4'-Fluoro-4-biphenylyl)-5-butyl-tetrahydropyran
2-(4'-Fluoro-4-biphenylyl)-5-pentyl-tetrahydropyran
2-(4'-Fluoro-4-biphenylyl)-5-hexyl-tetrahydropyran
2-(4'-Fluoro-4-biphenylyl)-5-heptyl-tetrahydropyran
2-(4'-Fluoro-4-biphenylyl)-5-octyl-tetrahydropyran
2-Propyl-5-p-fluorophenyl-tetrahydropyran
2-Butyl-5-p-fluorophenyl-tetrahydropyran
2-Pentyl-5-p-fluorophenyl-tetrahydropyran
2-Hexyl-5-p-fluorophenyl-tetrahydropyran
2-Heptyl-5-p-fluorophenyl-tetrahydropyran
2-Octyl-5-p-fluorophenyl-tetrahydropyran
2-Oxo-3-p-fluorophenyl-6-propyl-tetrahydropyran
2-Oxo-3-p-fluorophenyl-6-butyl-tetrahydropyran
2-Oxo-3-p-fluorophenyl-6-pentyl-tetrahydropyran
2-Oxo-3-p-fluorophenyl-6-hexyl-tetrahydropyran
2-Oxo-3-p-fluorophenyl-6-heptyl-tetrahydropyran
2-Oxo-3-p-fluorophenyl-6-octyl-tetrahydropyran
2-Propyl-5-(4'-fluoro-4-biphenylyl)-tetrahydropyran
2-Butyl-5-(4'-fluoro-4-biphenylyl)-tetrahydropyran
2-Pentyl-5-(4'-fluoro-4-biphenylyl)-tetrahydropyran
2-Hexyl-5-(4'-fluoro-4-biphenylyl)-tetrahydropyran
2-Heptyl-5-(4'-fluoro-4-biphenylyl)-tetrahydropyran
2-Octyl-5-(4'-fluoro-4-biphenylyl)-tetrahydropyran

EXAMPLE 12

A mixture of 2.94 g of 2-fluoro-4-(5-pentyl-2-tetrahydropyranyl)benzoic acid [obtainable by reaction of 2-m-fluorophenyl-5-pentyltetrahydropyran with acetyl chloride/ZnCl$_2$ to give 2-(4-acetyl-3-fluorophenyl)-5-pentyltetrahydropyran and degradation with Br$_2$KOH], 1.42 g of trans-4-propylcyclohexanol and 2.06 g of dicyclohexylcarbodiimide in 50 ml of diethyl ether is boiled for 6 hours. After cooling, the mixture is filtered, worked up as usual and trans-4-propylcyclohexyl 2-fluoro-4-(5-pentyl-2-tetrahydropyranyl)benzoate is obtained.

The following are obtained analogously:
Trans-4-methoxymethylcyclohexyl 4-(5-propyl-2-tetrahydropyranyl)benzoate
p-2-Methoxyethoxyphenyl 4-(5-pentyl-2-tetrahydropyranyl)benzoate
2,3,5,6-Tetrafluorophenyl 4-(5-pentyl-2-tetrahydropyranyl)benzoate
1-Propyl-4-piperidyl 4-(5-pentyl-2-tetrahydropyranyl)benzoate
1,4-Bicyclo[2.2.2]octyl 4-(5-pentyl-2-tetrahydropyranyl)benzoate
5-Methoxy-2-pyrimidinyl 4-(5-pentyl-2-tetrahydropyranyl)benzoate.

EXAMPLE 13

27.6 g of p-(5-pentyl-2-tetrahydropyranyl)benzoic acid (obtainable by reaction of 2-phenyl-5-pentyltetrahydropyran with acetyl chloride/AlCl$_3$ to give 2-p-acetylphenyl-5-pentyltetrahydropyran and degradation with bromine/KOH) are boiled with 24 g of SOCl$_2$ for 1 hour, and the mixture is evaporated, the crude acid chloride obtained is dissolved in 150 ml of toluene, 8 ml of pyridine and 16.6 g of trans-4-pentylcyclohexanol are added, and the mixture is boiled for two hours. After cooling and working up as usual, trans-4-pentylcyclohexyl p-(5-pentyl-2-tetrahydropyranyl)benzoate is obtained.

EXAMPLE 14

A mixture of 1.2 g of 2-propyl-1,3-propanediol, 2.2 g of 5-formyl-2-p-methoxyphenyltetrahydropyran [obtainable by reaction of diethyl ethylenedioxymethylmalonate with ω-bromo-p-methoxypropiophenone to give diethyl 2-ethylenedioxymethyl-2-(3-oxo-3-p-methoxyphenylpropyl)malonate, NaBH$_4$ reduction to the alcohol, hydrolysis, decarboxylation and lactonization to give 2-oxo-3-ethylenedioxymethyl-6-p-methoxyphenyltetrahydropyran, reduction with LiAlH$_4$ to the diol, and cyclization with p-toluenesulfonic acid with simultaneous cleavage of the acetal], 0.01 g of p-toluenesulfonic acid and 15 ml of toluene is boiled under a water separator for 3 hours, and the mixture is cooled, washed with water and evaporated. 2-p-Methoxyphenyl-5-(trans-5-propyl-1,3-dioxan-2-yl)tetrahydropyran is obtained.

The following are obtained analogously:
2-p-Methoxyphenyl-5-(trans-5-butyl-1,3-dioxan-2-yl)tetrahydropyran
2-p-Methoxyphenyl-5-(trans-5-pentyl-1,3-dioxan-2-yl)tetrahydropyran
2-p-Methoxyphenyl-5-(trans-5-hexyl-1,3-dioxan-2-yl)tetrahydropyran
2-p-Methoxyphenyl-5-(trans-5-heptyl-1,3-dioxan-2-yl)tetrahydropyran
2-p-Methoxyphenyl-5-(trans-5-octyl-1,3-dioxan-2-yl)tetrahydropyran.

EXAMPLE 15

65 g of POCl$_3$ are added dropwise, with stirring, to a solution of 29.3 g of 2-fluoro-4-(5-pentyl-2-tetrahydropyranyl)benzamide (obtainable from the acid chloride and NH$_3$) in 500 ml of DMF at 50°. After stirring for a further one hour, the mixture is poured onto ice, worked up as usual and 2-fluoro-4-(5-pentyl-2-tetrahydropyranyl)benzonitrile is obtained.

The following are obtained analogously:
2-Fluoro-4-(5-propyl-2-tetrahydropyranyl)benzonitrile
2-Fluoro-4-(5-butyl-2-tetrahydropyranyl)benzonitrile
2-Fluoro-4-(5-pentyl-2-tetrahydropyranyl)benzonitrile
2-Fluoro-4-(5-hexyl-2-tetrahydropyranyl)benzonitrile
2-Fluoro-4-(5-heptyl-2-tetrahydropyranyl)benzonitrile
2-Fluoro-4-(5-octyl-2-tetrahydropyranyl)benzonitrile

EXAMPLE 16

A solution of 29.5 g of p-(5-pentyl-2-tetrahydropyranyl)benzoyl chloride and 8 g of sulfamide in 500 ml of tetramethylene sulfone is heated at 120° for 4 hours, evaporated and worked up as usual. 2-p-cyanophenyl-5-pentyltetrahydropyran is obtained.

The other compounds indicated in Example 8 are obtainable analogously.

EXAMPLE 17

A mixture of 24.8 g of 2-p-hydroxyphenyl-5-pentyltetrahydropyran (obtainable by diazotization of 2-p-aminophenyl-5-pentyltetrahydropyran and hydrolysis), 6.9 g of K$_2$CO$_3$, 25 g of hexyl iodide and 250 ml of DMF is heated, with stirring, at 80° for 16 hours, then cooled and worked up as usual. 2-p-Hexoxyphenyl-5-pentyltetrahydropyran is obtained.

The following are obtained analogously:
2-p-Butoxyphenyl-5-propyl-tetrahydropyran 2-p-Butoxyphenyl-5-butyl-tetrahydropyran
2-p-Butoxyphenyl-5-pentyl-tetrahydropyran
2-p-Butoxyphenyl-5-hexyl-tetrahydropyran
2-p-Butoxyphenyl-5-heptyl-tetrahydropyran
2-p-Butoxyphenyl-5-octyl-tetrahydropyran
2-p-Pentoxyphenyl-5-propyl-tetrahydropyran
2-p-Pentoxyphenyl-5-butyl-tetrahydropyran
2-p-Pentoxyphenyl-5-pentyl-tetrahydropyran
2-p-Pentoxyphenyl-5-hexyl-tetrahydropyran
2-p-Pentoxyphenyl-5-heptyl-tetrahydropyran
2-p-Pentoxyphenyl-5-octyl-tetrahydropyran
2-p-Hexoxyphenyl-5-propyl-tetrahydropyran
2-p-Hexoxyphenyl-5-butyl-tetrahydropyran
2-p-Hexoxyphenyl-5-hexyl-tetrahydropyran
2-p-Hexoxyphenyl-5-heptyl-tetrahydropyran
2-p-Hexoxyphenyl-5-octyl-tetrahydropyran

EXAMPLE 18

A mixture of 31.1 g of 2-p-bromophenyl-5-pentyltetrahydropyran, 10 g of $Cu_2(CN)_2$, 120 ml of pyridine and 60 ml of N-methylpyrrolidone is heated at 150° for 2 hours. The mixture is cooled, a solution of 120 g of $FeCl_3.6H_2O$ in 600 ml of 20% hydrochloric acid is added, the mixture is heated, with stirring, at 70° for 1.5 hours, and worked up as usual, and 2-p-cyanophenyl-5-pentyltetrahydropyran is obtained.

The other compounds indicated in Example 8 are obtainable analogously.

Examples of dielectrics according to the invention, which contain at least one compound of the formula I follow:

EXAMPLE A

A mixture of
15% of 2-p-cyanophenyl-5-propyltetrahydropyran
27% of 2-p-ethylphenyl-5-propyltetrahydropyran
10% of trans-1-p-ethoxyphenyl-4-propylcyclohexane
7% of 4-cyano-4'-(trans-4-pentylcyclohexyl)biphenyl
9% of 1-(trans-4-propylcyclohexyl)-2-(p-trans-4-propylcyclohexylphenyl)ethane
8% of 4-ethyl-4'-(trans-4-pentylcyclohexyl)biphenyl
10% of 4-(trans-4-pentylcyclohexyl)-4'-(trans-4-propylcyclohexyl)biphenyl and
14% of p-trans-4-propylcyclohexylphenyl trans-4-butylcyclohexanecarboxylate
exhibits a c.p. of 85°.

EXAMPLE B

A mixture of
17% of 2-p-cyanophenyl-5-propyltetrahydropyran
23% of p-trans-4-butylcyclohexylbenzonitrile
14% of 4-ethyl-4'-cyanobiphenyl
26% of 4-butyl-4'-cyanobiphenyl
8% of 4,4'-bis(trans-4-propylcyclohexyl)biphenyl and
12% of p-cyanophenyl p-pentylbenzoate
exhibits a c.p. of 61°.

EXAMPLE C (MIXTURE WITH NEGATIVE DIELECTRIC ANISOTROPY)

A mixture of
25% of 2-p-ethoxyphenyl-5-propyltetrahydropyran
25% of trans-1-p-butoxyphenyl-4-propylcyclohexane
15% of p-pentylphenyl trans-4-pentylcyclohexanecarboxylate
15% of p-ethoxyphenyl trans-4-propylcyclohexanecarboxylate
10% of 4-(trans-4-pentylcyclohexyl)-4'-(trans-4-propylcyclohexyl)biphenyl and
10% of 4-butyl-2-cyanophenyl p-trans-4-propylcyclohexylbenzoate
exhibits a c.p. of 73°.

EXAMPLE D (MATRIX FOR DICHROIC DYESTUFFS)

A mixture of
15% of 2-p-cyanophenyl-5-propyltetrahydropyran
14% of 2-p-cyanophenyl-5-butyltetrahydropyran
18% of p-trans-4-propylcyclohexylbenzonitrile
25% of p-trans-4-butylcyclohexylbenzonitrile
7% of 4-cyano-4'-(trans-4-pentylcyclohexyl)biphenyl
6% of 4-p-cyanophenyl-4'-pentylbiphenyl
7% of 4-(trans-4-pentylcyclohexyl)-4'-(trans-4-propylcyclohexyl)biphenyl and
8% of p-trans-4-propylcyclohexylphenyl trans-4-butylcyclohexanecarboxylate
exhibits a c.p. of 86°.

EXAMPLE E

The dyestuff exhibits an order parameter of 0.75 in a mixture of
98% of matrix according to Example D and
2% of 1,5-dihydroxy-2,6-bis(trans-4-propylcyclohexyl)-4,8-diaminoanthraquinone.

EXAMPLE F

A mixture of
8% of 2-oxo-3-heptyl-6-p-pentylphenyltetrahydropyran
21% of trans-1-p-ethoxyphenyl-4-propylcyclohexane
18% of trans-1-p-butoxyphenyl-4-propylcyclohexane
41% of p-trans-4-propylcyclohexylphenyl butyrate and
12% of 4-(trans-4-pentylcyclohexyl)-4'-(trans-4-propylcyclohexyl)biphenyl
exhibits a m.p. of −10° and a c.p. of 59°.

The preceding examples can be repeated with similar success by substituting the generically or specificially described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A liquid-crystal dielectric useful for electrooptical display elements comprising at least two liquid crystal components, wherein at least one component is a compound of the formula

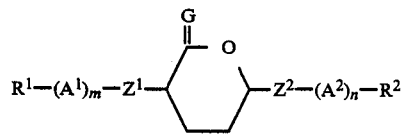

wherein
G is $H_2$ or =O;
$R^1$ and $R^2$ each independently is alkyl of 1–10 C-atoms; alkyl of 1–10 C atoms wherein one or two non-adjacent $CH_2$ groups are replaced by O atoms; F; Cl; Br; or CN; and $R^2$ can also be H;
$A^1$ and $A^2$ each independently is 1,4-phenylene, 1,4-cyclohexylene, 1,3-dioxane-2,5-diyl, piperidine-1,4-diyl, 1,4-bicyclo[2.2.2]octylene or pyrimidine-2,5- diyl or one of these groups substituted by 1–4 F atoms;

Z¹ and Z² each independently is —CO—O—, —O—CO—, CH₂CH₂—, —OCH₂—, —CH₂O—, or a single bond; and m and n each is 0, 1, 2, or 3, but (m+n) is at least 1 and at most 3, it being possible, when m is 2 or 3, for the groups A¹ and, when n is 2 or 3, for the groups A² each to be identical or different from one another, with the proviso that when —(A²)ₙ—R² is OR, wherein R is H or alkyl, Z¹ and Z² are single bonds, and G is H₂, then R¹-(A¹)ₘ— is not 4-cyanophenyl, 4-alkylphenyl and 4-alkylcyclohexyl.

2. A dielectric of claim 1 wherein said compound is of the formula

R¹—Phe—Z¹—A—Z²—R²

R¹—Cy—Z¹—A—Z²—R²

R¹—Dio—Z¹—A—Z²—R²

R¹—Pip—Z¹—A—Z²—R²

R¹—Bi—Z¹—A—Z²—R², or

R¹—Pyr—Z¹—A—Z²—R² wherein "A" deontes 2-G-tetrahydropyran-3,6-diyl; "Phe" denotes 1,4-phenylene; "Cy" denotes 1,4-cyclohexylene; "Dio" denotes 1,3-dioxane-2,5-diyl; "Bi" denotes bicyclo[2.2.2]octylene; "Pip" denotes piperidine-1,4-diyl; and "Pyr" denotes pyrimidine-2-5-diyl.

3. A dielectric of claim 1 wherein said compound is of the formula

R¹—Z¹—A—Z²—Phe—R²

R¹—Z¹—A—Z²—Cy—R²

R¹—Z¹—A—Z²—Dio—R²

R¹—Z¹—A—Z²—Pip—R²

R¹—Z¹—A—Z²—Bi—R², or

R¹—Z¹—A—Z²—Pyr—R² wherein "A" deontes 2-G-tetrahydropyran-3,6-diyl; "Phe" denotes 1,4-phenylene; "Cy" denotes 1,4-cyclohexylene; "Dio" denotes 1,3-dioxane-2,5-diyl; "Bi" denotes bicyclo[2.2.2]octylene; "Pip" denotes piperidine-1,4-diyl; and "Pyr" denotes pyrimidine-2-5-diyl.

4. A dielectric of claim 1 wherein said compound is of the formula R¹—Z¹—A—Z²—Phe—R².

5. A dielectric of claim 1 wherein said compound is of the formula

R¹—Phe—Phe—Z¹—A—Z²—R²

R¹—Phe—Cy—Z¹—A—Z²—R²

R¹—Cy—Phe—Z¹—A—Z²—R², or

R¹—Cy—Cy—Z¹—A—Z²—R² wherein "A" denotes 2-G-tetrahydropyan-3,6-diyl; "Phe" denotes 1,4-phenylene; "Cy" denotes 1,4-cyclohexylene.

6. A dielectric of claim 1 wherein said compound is of the formula

R¹—Phe—Z¹—A—Z²—Phe—R²

R¹—Phe—Z¹—A—Z²—Cy—R²

R¹—Cy—Z¹—A—Z²—Phe—R², or

R¹—Cy—Z¹—A—Z—Cy—R² wherein "A" denotes 2-G-tetrahydropyran-3,6-diyl; "Phe" denotes 1,4-phenylene and; "Cy" denotes 1,4-cyclohexylene.

7. A dielectric of claim 1 wherein said compound is of the formula

R¹—Z¹—A—Z²—Phe—Phe—R²

R¹—Z¹—A—Z²—Phe—Cy—R²

R¹—Z¹—A—Z²—Cy—Phe—R², or

R¹—Z¹—A—Z²—Cy—Cy—R² wherein "A" denotes 2-G-tetrahydropyran-3,6-diyl; "Phe" denotes 1,4-phenylene and; "Cy" denotes 1,4-cyclohexylene.

8. A dielectric of claim 1 wherein said compound is of the formula

R¹—Phe—Phe—Phe—Z¹—A—Z²—R²

R¹—Phe—Phe—Cy—Z¹—A—Z²—R²

R¹—Phe—Cy—Phe—Z¹—A—Z²—R²

R¹—Phe—Cy—Cy—Z¹—A—Z²—R²

R¹—Cy—Phe—Phe—Z¹—A—Z²—R²

R¹—Cy—Phe—Cy—Z¹—A—Z²—R²

R¹—Cy—Cy—Phe—Z¹—A—Z²—R², or

R¹—Cy—Cy—Cy—Z¹—A—Z²—R² wherein "A" denotes 2-G-tetrahydropyran-3,6-diyl; "Phe" denotes 1,4-phenylene and; "Cy" denotes 1,4-cyclohexylene.

9. A dielectric of claim 1 wherein said compound is of the formula

R¹—Phe—Phe—Z¹—A—Z²—Phe—R²

R¹—Phe—Phe—Z¹—A—Z²—Cy—R²

R¹—Phe—Cy—Z¹—A—Z²—Phe—R²

R¹—Phe—Cy—Z¹—A—Z²—Cy—R²

R¹—Cy—Phe—Z¹—A—R²—Phe—R²

R¹—Cy—Phe—Z¹—A—Z²—Cy—R²

R¹—Cy—Cy—Z¹—A—Z²—Phe—R², or

R¹—Cy—Cy—Z¹—A—Z²—Cy—R² wherein "A" denotes 2-G-tetrahydropyran-3,6-diyl; "Phe" denotes 1,4-phenylene and; "Cy" denotes 1,4-cyclohexylene.

10. A dielectric of claim 1 wherein said compound is of the formula

R¹—Phe—Z¹—A—Z²—Phe—Phe—R²

R¹—Phe—Z¹—A—Z²—Phe—Cy—R²

R¹—Phe—Z¹—A—Z²—Cy—Phe—R²

R¹—Phe—Z¹—A—Z²ᵈ—Cy—Cy—R²

$R^1$—Cy—$Z^1$—A—$Z^2$—Phe—Phe—$R^2$ $R^1$—Cy—$Z^1$—A—$Z^2$—Phe—Cy—$R^2$ $R^1$—Cy—$Z^1$—A—$Z^2$—Cy—Phe—$R^2$, or $R^1$—Cy—$Z^1$—A—$Z^2$—Cy—Cy—$R^2$ wherein "A" denotes 2-G-tetrahydropyran-3,6-diyl; "Phe" denotes 1,4-phenylene and; "Cy" denotes 1,4-cyclohexylene.

11. A dielectric of claim 1 wherein said compound is of the formula $R^1$—$Z^1$—A—$Z^2$—Phe—Phe—Phe—$R^2$ $R^1$—$Z^1$—A—$Z^2$—Phe—Phe—Cy—$R^2$ $R^1$—$Z^1$—A—$Z^2$—Phe—Cy—Phe—$R^2$ $R^1$;13 $Z^1$—A—$Z^2$—Phe—Cy—Cy—$R^2$ $R^1$—$Z^1$—A—$Z^2$—Cy—Phe—Phe—$R^2$ $R^1$—$Z^1$—A—$Z^2$—Cy—Phe—Cy—$R^2$ $R^1$—$Z^1$—A—$Z^2$—Cy—Cy—Phe—$R^2$, or $R^1$—$Z^1$—A—$Z^2$—Cy—Cy—Cy—$R^2$ wherein "A" denotes 2-G-tetrahydropyran-3,6-diyl; "Phe" denotes 1,4-phenylene and; "Cy" denotes 1,4-cyclohexylene.

12. A dielectric of claim 1 wherein said compound is of the formula $R^1$—$Z^1$—A—$Z^2$Phe—Phe—$R^2$, or $R^1$—$Z^1$—A—$Z^2$Phe—Phe—Cy—$R^2$, wherein "A" denotes 2-G-tetrahydropyran-3,6-diyl; "Phe" denotes 1,4-phenylene and; "Cy" denotes 1,4-cyclohexylene.

13. A dielectric of claim 1 wherein in said compound G is $H_2$ and $Z^1$ and $Z^2$ are single bonds.

14. A dielectric of claim 1 wherein in said compound m is 0 and n is 1.

15. A dielectric of claim 1 wherein said compound is of the formula $R^1$—A—Phe—CN $R^1$—A—Phe—Phe—$R^2$ or $R^1$—A—Phe—Phe—Cy—$R^2$ wherein "A" denotes 2-G-tetrahydropyran-3,6-diyl; "Phe" denotes 1,4-phenylene and; "Cy" denotes 1,4-cyclohexylene.

16. In an electrooptical display element comprising a liquid crystalline dielectric, the improvement wherein the dielectric is that of claim 1.

17. A liquid crystal dielectric useful for electrooptical display elements comprising at least two liquid crystal components, wherein at least one component is a compound of the formula $R^1$—A—Ph—COO—$A^2$—$R^2$ wherein $R^1$ and $R^2$ each independently is alkyl of 1–10 C-atoms; alkyl of 1–10 C atoms wherein one or two non-adjacent $CH_2$ groups are replaced by O atoms, F; Cl: Br; or CN; and $R^2$ can also be H;

A is 1-G-2-tetrahydropyran-3,6-diyl;

G is $H_2$ or =O;

Ph is 1,4-phenylene or 1,4-phenylene substituted by 1–4 F atoms; and $A^2$ is 1,4-phenylene, 1,4-cyclohexylene, 1,3-dioxane-2,5-diyl, piperidine-1,4-diyl, 1,4-bicyclo[2.2.2]octylene or pyrimidine-2,5-diyl or one of these groups substituted by 1–4 F atoms.

* * * * *

UNITED STATES PATENT AND TRADEMARK OFFICE
CERTIFICATE OF CORRECTION

PATENT NO. : 4,818,431

DATED : April 4, 1989

INVENTOR(S) : Rudolf Eidenschink et al

It is certified that error appears in the above-identified patent and that said Letters Patent is hereby corrected as shown below:

Column 27, line 32: reads "piperidine-1,4-diyl; and "Pyr" denotes pyrimidine-2-5-"

should read -- piperidine-1,4-diyl; and "Pyr" denotes pyrimidine-2,5- --

Column 27, line 52: reads "piperidine-1,4-diyl; and "Pyr" denotes pyrimidine-2-5- -- should read -- piperidine-1,4-diyl; and "Pyr" denotes pyrimidine-2,5- --

Column 27, line 68: reads ""Phe" denotes 1,4-phenylene; "Cy" denotes 1,4- "

should read -- "Phe" denotes 1,4-phenylene; "Cy" denotes 1,4- --

Column 29, line 19: reads "$R^1;13Z^1-A-Z^2-Phe-Cy-Cy-R^2$"

should read -- $R^1-Z^1-A-Z^2-Phe-Cy-Cy-R^2$ --

UNITED STATES PATENT AND TRADEMARK OFFICE
CERTIFICATE OF CORRECTION

PATENT NO. : 4,818,431

DATED : April 4, 1989

INVENTOR(S) : Rudolf Eidenschink et al

It is certified that error appears in the above-identified patent and that said Letters Patent is hereby corrected as shown below:

Column 29, line 35: reads "$R^1-Z^1-A-Z^2Phe-Phe-R^2$, or"

should read -- $R^1-Z^1-A-Z^2-Phe-Phe-R^2$, or --

Column 29, line 37: reads "$R^1-Z^1-A-Z^2Phe-Phe-Cy-R^2$,"

should read -- $R^1-Z^1-A-Z^2-Phe-Phe-Cy-R^2$, --

Signed and Sealed this

Twenty-seventh Day of February, 1990

*Attest:*

JEFFREY M. SAMUELS

*Attesting Officer*  *Acting Commissioner of Patents and Trademarks*